United States Patent
Belli et al.

(10) Patent No.: US 10,563,262 B2
(45) Date of Patent: Feb. 18, 2020

(54) BIOMARKERS OF TRAUMATIC BRAIN INJURY

(71) Applicant: THE UNIVERSITY OF BIRMINGHAM, Birmingham (GB)

(72) Inventors: Antonio Belli, East Wellow Hampshire (GB); Valentina Di Pietro, West Midlands (GB)

(73) Assignee: THE UNIVERSITY OF BIRMINGHAM, Birmingham (GB)

( * ) Notice: Subject to any disclaimer, the term of this patent is extended or adjusted under 35 U.S.C. 154(b) by 0 days.

(21) Appl. No.: 15/852,128

(22) Filed: Dec. 22, 2017

(65) Prior Publication Data

US 2018/0127828 A1    May 10, 2018

Related U.S. Application Data

(63) Continuation-in-part of application No. PCT/GB2017/050231, filed on Jan. 30, 2017.

(30) Foreign Application Priority Data

Mar. 8, 2016 (GB) .................................. 1603967.9

(51) Int. Cl.
| | | |
|---|---|---|
| C12Q 1/68 | (2018.01) | |
| A61K 31/713 | (2006.01) | |
| C12N 15/113 | (2010.01) | |
| C12Q 1/6883 | (2018.01) | |

(52) U.S. Cl.
CPC ..... *C12Q 1/6883* (2013.01); *C12Q 2600/106* (2013.01); *C12Q 2600/118* (2013.01); *C12Q 2600/178* (2013.01)

(58) Field of Classification Search
None
See application file for complete search history.

(56) References Cited

U.S. PATENT DOCUMENTS

2015/0344954 A1    12/2015   Patel et al.

FOREIGN PATENT DOCUMENTS

| WO | WO-2011/032155 A2 | 3/2011 |
| WO | WO-2011/032155 A3 | 3/2011 |
| WO | WO-2015/134551 A1 | 9/2015 |
| WO | WO-2015/164431 A2 | 10/2015 |
| WO | WO-2015/164431 A3 | 10/2015 |
| WO | WO-2015/196191 A1 | 12/2015 |
| WO | WO-2016/153549 A1 | 9/2016 |
| WO | WO-2017/019976 A2 | 2/2017 |
| WO | WO-2017/019976 A3 | 2/2017 |
| WO | 2018175422 A1 | 9/2018 |
| WO | 2018175941 A1 | 9/2018 |

OTHER PUBLICATIONS

Balakathiresan, N. et al. (May 2012, e-published Apr. 13, 2012). "MicroRNA let-7i is a promising serum biomarker for blast-induced traumatic brain injury," *J Neurotrauma* 29(7):1379-1387.
Dipietro, V. et al. (Jun. 2017, Apr. 10, 2017). "MicroRNAs as Novel Biomarkers for the Diagnosis and Prognosis of Mild and Severe Traumatic Brain Injury," *J Neurotrauma* 34(11):1948-1956.
Lei, P. et al. (Aug. 11, 2009, e-published Jun. 6, 2009). "Microarray based analysis of microRNA expression in rat cerebral cortex after traumatic brain injury," *Brain Res* 1284:191-201.
Redell, J.B. et al. (Dec. 2010, e-published Nov. 23, 2010). "Human traumatic brain injury alters plasma microRNA levels," *J Neurotrauma* 27(12):2147-2156.
Redell, J.B. et al. (Feb. 2011, e-published Dec. 8, 2010). "Altered expression of miRNA-21 and its targets in the hippocampus after traumatic brain injury," *J Neurosci Res* 89(2):212-221.
Reis, C. et al. (May 26, 2015). "What's New in Traumatic Brain Injury: Update on Tracking, Monitoring and Treatment," *Int J Mol Sci* 16(6):11903-11965.
Sharma, A. et al. (Nov. 7, 2014). "Identification of serum microRNA signatures for diagnosis of mild traumatic brain injury in a closed head injury model," *PLoS One* 9(11):e112019.
Truettner, J.S. et al. (Sep. 2011, e-published Apr. 20, 2011). "Therapeutic hypothermia alters microRNA responses to traumatic brain injury in rats," *J Cereb Blood Flow Metab* 31(9):1897-1907.
International Search Report dated Jun. 13, 2017, for PCT Application No. PCT/GB2017/050231, filed Jan. 30, 2017, 10 pages.
EP Application No. 17703217.4 Examination Report dated Oct. 2, 2019.
Lim et al. "MicroRNAs in Cerebral Ischemia", Translational Stroke Research, Jul. 31, 2010 (Jul. 31, 2010), pp. 287-383, vol. 1, No. 4.
Wang et al., "Differential expression of circulating microRNAs in blood and haematoma samples from patients with intracerebral haemorrhage", Journal of International Medical Research, Mar. 28, 2016 (Mar. 28, 2016), pp. 419-432, vol. 44, No. 3.
Han et al., "Diagnostic value of elevated serum miRNA-I 43 levels in sepsis", Journal of International Medical Research, May 25, 2016 (May 25, 2016), pp. 875-881, vol. 44, No. 4.

*Primary Examiner* — Tracy Vivlemore
(74) *Attorney, Agent, or Firm* — FisherBroyles, LLP; James W. Hill

(57) ABSTRACT

Provided is a method of diagnosing and/or monitoring mild traumatic brain injury (mTBI) or concussion in a subject. The method comprises determining a level of at least one miRNA in a saliva sample from the subject. Also provided is a sensor element, a detection system, composition and a kit for diagnosing and/or monitoring TBI, and a method of determining an appropriate treatment for a subject with suspected mTBI or concussion.

14 Claims, 8 Drawing Sheets

Specification includes a Sequence Listing.

BIOMARKERS OF TRAUMATIC BRAIN INJURY

CROSS-REFERENCE TO RELATED APPLICATIONS

The present application is a Continuation-in-Part of PCT International Application PCT/GB2017/050231, filed on Jan. 30, 2017, which claims the benefit of priority under 35 U.S.C. § 119 (e) to GB Patent Application No. 1603967.9, filed Mar. 8, 2016.

REFERENCE TO SEQUENCE LISTING

The present application contains a Sequence Listing in ASCII format. Said ASCII copy, created on Dec. 21, 2017, is named sequence listing.txt and is 10,436 bytes in size.

FIELD OF THE INVENTION

The present invention relates to compositions, kits, systems and methods for diagnosing and/or monitoring traumatic brain injury (TBI). More particularly, the present invention relates to the diagnosis and monitoring of TBI using miRNA biomarkers.

BACKGROUND TO THE INVENTION

Traumatic brain injury (TBI) is the leading cause of death and disability under the age of 45 years in Western countries. Its healthcare burden and social costs are expected to continue to rise and, by 2020, the World Health Organization projects TBI to become the third leading cause of disability worldwide.

Despite many studies, no reliable biomarkers have been found to assess the severity of TBI and predict recovery. This is especially true for mild TBI (mTBI), which remains currently difficult to assess in clinical practice. Although TBI patients are initially assessed by the Glasgow Coma Score (GCS) and neuroimaging techniques, which require costly equipment, the current diagnostic tools are lacking in the ability to precisely define and quantify the actual severity of the brain injury, thus leading to an easy detection of severe but not of mTBI, which represents the vast majority of cases (75-90%).

The correct diagnosis of mTBI is particularly important in patients, such as athletes, soldiers and children, who are at greater risk of repetitive mTBI and a catastrophic form of brain injury known as second impact syndrome (SIS) where the synergistic effects of repeated TBI result in profound damage and even death. Early diagnosis and evaluation of the severity of TBI thus becomes crucial for patients' wellbeing and ultimately saving their life.

The quest for TBI biomarkers has received significant impetus by the increased profile of sport concussion in the media. In the last few years many studies have focused on biomarkers that can support clinical decision making pitchside or in a sports clinic. However, protein biomarkers reported in the literature lack specificity or sensitivity, or are not detectable for some time after injury. This may be due to the fact that following concussion, which is a form of TBI, brain-derived compounds are only released in very small amounts and the blood-brain barrier remains mostly closed.

MicroRNAs (miRNAs) are an abundant class of highly conserved, non-coding RNA molecules of approximately 22 nucleotides in length that induce mRNA degradation, translational repression or both via pairing with partially complementary sites in the 3'UTR of target genes. The human genome encodes over 2,000 miRNAs, which may target about 60% of all genes. However, despite the abundance of miRNAs, their biomolecular functions and involvement in pathology remain to be fully elucidated. They play a central role in many biological processes including cell cycle, cell metabolism, apoptosis and immune responses, and are attracting increasing interest in clinical research as potential biomarkers for the detection, identification and classification of cancers and other disease states including neurodegenerative diseases.

The present invention was devised with these issues in mind.

SUMMARY

The disclosure provides methods and detection systems relating to diagnosing, monitoring, and treating traumatic brain injury (TBI) including mild traumatic brain injury (mTBI) in a human subject who has suffered an injury to the head by detecting one or more miRNA molecules in a biological sample from the subject. In the context of the following disclosure, the terms 'level' and 'amount' in reference to the level or amount of an miRNA molecule or molecules in a biological sample are used interchangeably.

In embodiments, the disclosure provides a method of diagnosing and/or monitoring mTBI in a subject, the method comprising determining a level of at least one miRNA in a saliva sample obtained from the subject, wherein the at least one miRNA is selected from the group consisting of miR-27b-3p, let-7i-5p, miR-142-3p, miR-107 and miR-135b-5p, or any combination thereof. In embodiments, an upregulated level of the at least one miRNA is indicative of mTBI. In embodiments, the subject is diagnosed as having mTBI if the level of the at least one miRNA is above a predetermined threshold or increased relative to a control. In embodiments, the predetermined threshold is equivalent to a fold change of 2 or more in the 2-delta delta CT (2-ΔΔCT) method. In embodiments, the at least one miRNA is miR-27b-3p. In embodiments, the at least one miRNA is let-7i-5p. In embodiments, the at least one miRNA is miR-142-3p. In embodiments, the at least one miRNA is miR-107. In embodiments, the at least one miRNA is miR-135b-5p.

In embodiments, the the method comprises determining a level of at least two miRNAs in a saliva sample obtained from the subject. In embodiments, the at least two miRNAs are selected from miR-27b-3p, let-7i-5p, miR-142-3p, miR-107 or miR-135b-5p. In embodiments, an upregulated level of the at least two miRNAs is indicative of mTBI. In embodiments, the subject is diagnosed as having mTBI if the level of the at least two miRNAs is above a predetermined threshold or increased relative to a control. In embodiments, the predetermined threshold is equivalent to a fold change of 1.5 or more in the 2-delta delta CT method.

In embodiments, the saliva sample is obtained 24 hours to 15 days after injury. In embodiments, the saliva sample is obtained 24 hours to 7 days after injury. In embodiments, the saliva sample is obtained 2 to 5 days after injury.

In embodiments, the method comprises determining a level of each of the miRNAs miR-27b-3p, let-7i-5p, miR-142-3p, miR-107 and miR-135b-5p.

In embodiments, the method further comprises determining a level of one or more additional miRNAs selected from let-7c-5p, let-7i-5p, miR-142-3p, miR-148a-3p, miR-15b-5p, miR-16-5p, miR-181a-5p, miR-20a-5p, miR-20b-5p, miR-221-3p, miR-24-3p, miR-27b-3p, miR-29a-3p, miR- 29c-3p, and miR-424-5p, miR-30a-5p, miR-107, miR-135b-5p, miR-199b-5p, miR-324-5p, or miR-652-3p.

The disclosure also provides a sensor element for a detection system for diagnosing and/or monitoring mTBI, the sensor element comprising a substrate functionalised with a probe specific for at least one of miR-27b-3p, let-7i-5p, miR-142-3p, miR-107 or miR-135b-5p. In embodiments, the probe comprises a nucleic acid able to bind to the at least one miRNA. In embodiments, the probe comprises a nucleic acid having at least 70% identity with a sequence which is the complement of the sequence of the target miRNA. In embodiments, the probe comprises a nucleic acid having at least 70% identity with a sequence which is the complement of SEQ ID NO: 25, 26, 35, 39 or 40.

The disclosure also provides a detection system for diagnosing and/or monitoring mTBI, comprising a sensor element as described herein, and a detection device capable of detecting the binding of a target miRNA to the probe. In embodiments, the detection system further comprises a means to determine whether the target miRNA is upregulated.

The disclosure also provides a method for determining a course of action for a subject suspected of having mTBI, comprising applying a saliva sample obtained from the subject to a detection system as described herein, if an upregulated level of the at least one miRNA is detected providing a treatment for mTBI.

The disclosure also provides a method of treating a subject with suspected mTBI, the method comprising i) determining whether an upregulated level of at least one miRNA selected from the group consisting of miR-27b-3p, let-7i-5p, miR-142-3p, miR-107 and miR-135b-5p is detectable in a saliva sample obtained from the subject, and ii) if an upregulated level of at least one miRNA is detected providing treatment for mTBI to the subject.

The disclosure also provides a method of detecting an miRNA in a saliva sample, the method comprising obtaining a saliva sample from a human subject, contacting the saliva sample with at least one oligonucleotide primer complementary to at least one miRNA selected from the group consisting of miR-27b-3p, let-7i-5p, miR-142-3p, miR-107 and miR-135b-5p, amplifying the at least one miRNA using a polymerase chain reaction, and detecting the amplified miRNA.

The disclosure also provides a method of diagnosing and treating mild traumatic brain injury (mTBI) in a human subject in need thereof, wherein the subject in need is one who has received an injury to the head, the method comprising detecting an amount of at least one miRNA in a saliva sample obtained from the subject, wherein the at least one miRNA is selected from the group consisting of miR-27b-3p, let-7i-5p, miR-142-3p, miR-107 and miR-135b-5p; identifying the subject as suffering from mTBI where the amount of the at least one miRNA is increased relative to a predetermined threshold value or relative to the amount of the miRNA in a control sample; and treating the subject identified as suffering from mTBI according to one or more of the following: subjecting the subject to a verbal, cognitive, motor, or optical test, or any combination of the foregoing, subjecting the subject to diagnostic imaging in the form of a CT or MRI, or a combination thereof, administering to the subject one or more neuroprotective therapies.

In embodiments, the saliva sample is obtained 24 hours to 15 days after the injury. In embodiments, the method further comprises obtaining one or more additional saliva samples from the subject at one or more additional times after the injury and repeating the detecting and amplifying steps for each additional sample. In embodiments, the one or more additional saliva samples is obtained at day 2, 3, 5, 7, 10, 14, or 15 after the injury. In embodiments, the detecting an amount of the at least one miRNA is performed using a PCR-based assay. In embodiments, the predetermined threshold is equivalent to a fold change of 1.5 or more using the 2-delta delta CT (2-ΔΔCT) method. In embodiments, the predetermined threshold is equivalent to a fold change of 2 or more using the 2-delta delta CT (2-ΔΔCT) method. In embodiments, the method comprises determining a level of at least two miRNAs in the saliva sample. In embodiments, the at least two miRNAs are selected from miR-27b-3p, let-7i-5p, miR-142-3p, miR-107 or miR-135b-5p. In embodiments, the method comprises determining the amount of each of the miRNAs miR-27b-3p, let-7i-5p, miR-142-3p, miR-107 and miR-135b-5p. In embodiments, the method further comprises determining the amount of one or more additional miRNAs selected from let-7c-5p, let-7i-5p, miR-142-3p, miR-148a-3p, miR-15b-5p, miR-16-5p, miR-181a-5p, miR-20a-5p, miR-20b-5p, miR-221-3p, miR-24-3p, miR-27b-3p, miR-29a-3p, miR-29c-3p, miR-424-5p, miR-30a-5p, miR-107, miR-135b-5p, miR-199b-5p, miR-324-5p, and miR-652-3p.

* significantly different from HV

Figure 5:
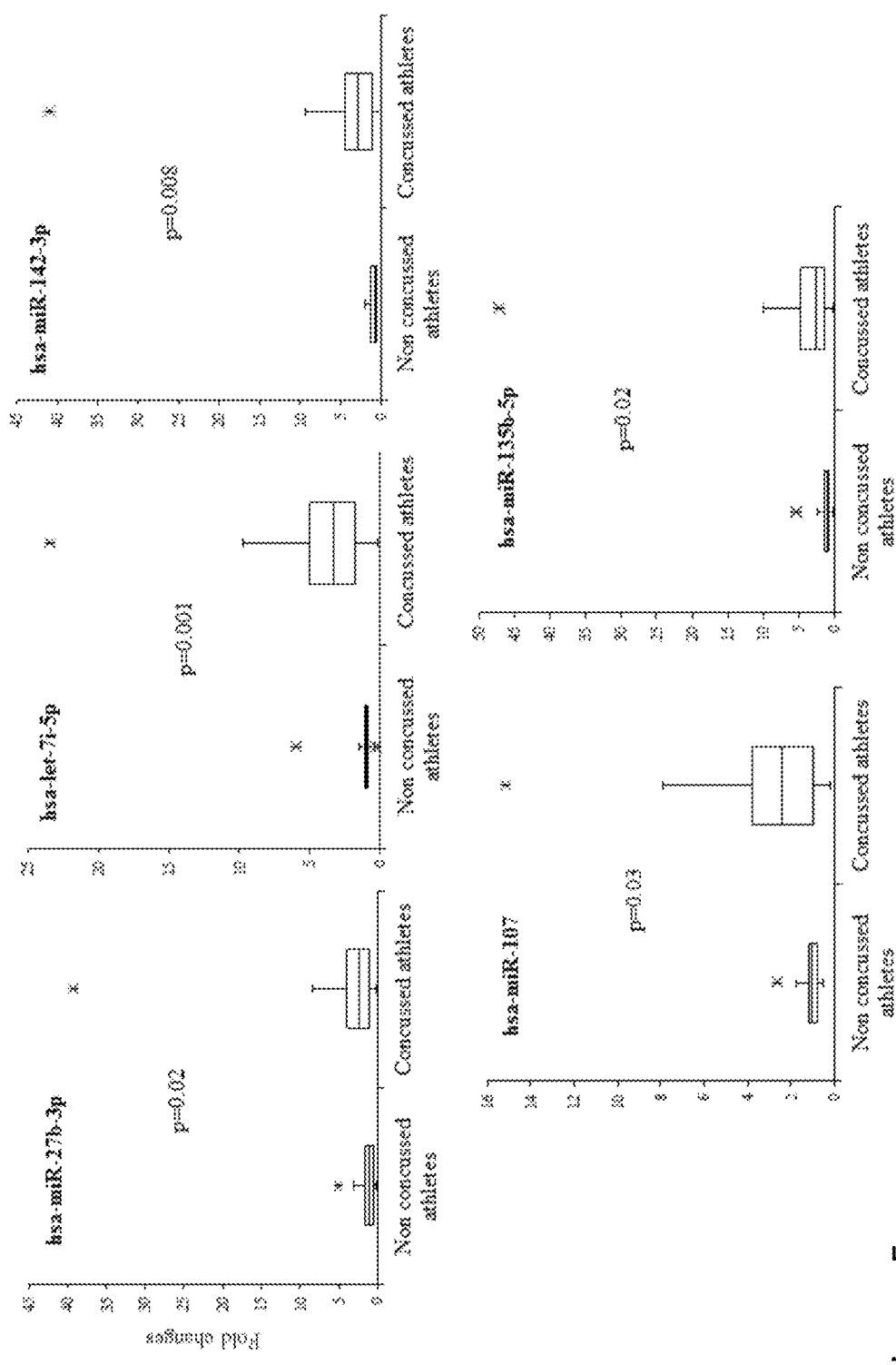

FIG. 5: Boxplot of relative expression of the 5 microRNAs which showed a significant upregulation (p<0.05) in the validation group and assessed by RT-PCR. A non parametric test (Mann-Whitney U test) was used to compare the level of microRNAs in the two independent groups.

Figure 6:
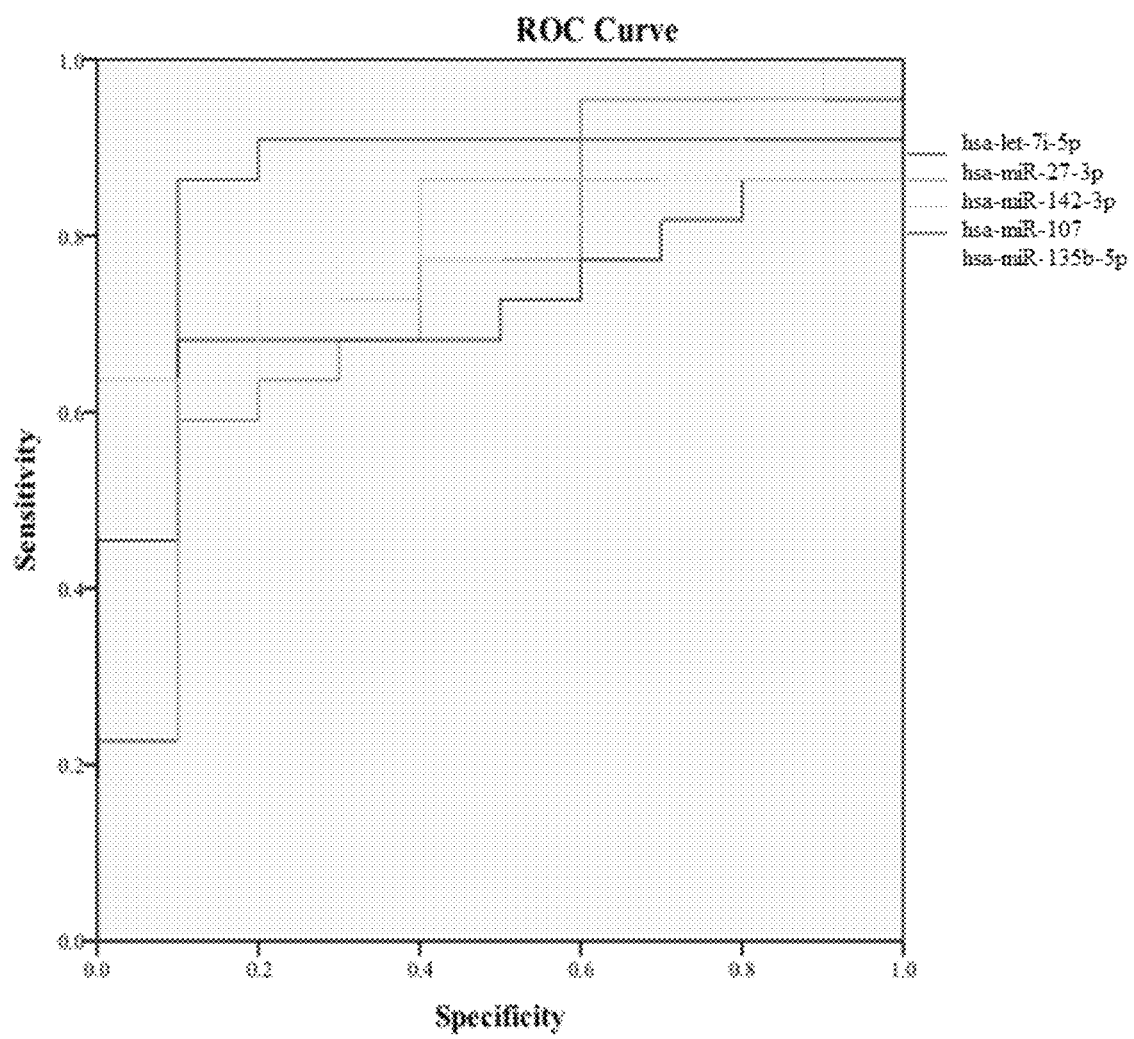

FIG. 6: Receiver-operating characteristic (ROC) curve and corresponding area under the curve (AUC) statistics for biomarkers identified in the validation cohort.

DETAILED DESCRIPTION

The present invention provides methods of diagnosing or monitoring traumatic brain injury (TBI) in a subject, as well as methods for treating a subject identified as suffering from TBI.

According to a first aspect of the invention, there is provided a method for diagnosing and/or monitoring traumatic brain injury (TBI) in a subject, the method comprising detecting the presence of and/or determining a level of at least one miRNA in a sample from the subject.

The at least one miRNA (also referred to herein as "miR") may be selected from the group consisting of miR-505, miR-203, miR-654-3p, miR-655, miR-184, miR-301b, miR-425-5p, miR-502, miR-21, miR-let-7g, miR-335, miR-126*, miR-193a-5p, miR-144*, miR-190, miR-194, miR-365, miR-590-3p, miR-624, miR-625*, miR-671-3p, hsa-let-7c-5p, hsa-let-7i-5p miR-142-3p, miR-148a-3p, miR-15b-5p, miR-16-5p, miR-181a-5p, miR-20a-5p, miR-20b-5p, miR-221-3p, miR-24-3p, miR-27b-3p, miR-29a-3p, miR-29c-3p, miR-424-5p, miR-30a-5p; miR-107; miR-135b-5p; miR-199b-5p; miR-324-5p; miR-652-3p; miR-10a, miR-132, miR-223, miR-143, miR-148b, miR-18a, miR-192, miR-429, miR-618, miR-95, miR-130a, miR-152, miR-27b, miR-301, miR-326, miR-345, miR-361, miR-422a, miR-579, miR-642, miR-99a, miR-520D-3p and miR-629. These miRNAs may be referred to herein as miRNAs of interest or target miRNAs.

In some embodiments, the at least one miRNA is selected from the group consisting of miR-505, miR-203, miR-654-3p, miR-655, miR-184, miR-301b, miR-425-5p, miR-502, miR-21, miR-let-7g, miR-335, hsa-miR-126*, miR-193a-5p, miR-144*, miR-190, miR-194, miR-365, miR-590-3p, miR-624, miR-625*, and miR-671-3p. These microRNAs have been found to be biomarkers expressed in all TBI patients (mild or severe).

In some embodiments, the at least one miRNA is selected from the group consisting of miR-505, miR-203, miR-654-3p, miR-655, miR-184, miR-301b, miR-425-5p, miR-502, miR-21, miR-let-7g and miR-335.

In some embodiments, the at least one miRNA is selected from the group consisting of let-7c-5p, let-7i-5p, miR-142-3p, miR-148a-3p, miR-15b-5p, miR-16-5p, miR-181a-5p, miR-20a-5p, miR-20b-5p, miR-221-3p, miR-24-3p, miR-27b-3p, miR-29a-3p, miR-29c-3p, and miR-424-5p; miR-30a-5p; miR-107; miR-135b-5p; miR-199b-5p; miR-324-5p; miR-652-3p.

In some embodiments, the at least one miRNA is selected from the group consisting of miR-27b-3p, let-7i-5p, miR-142-3p, miR-107 and miR-135b-5p.

In some embodiments, the at least one miRNA is selected from the group consisting of miR-10a, miR-132, miR-223, miR-143, miR-148b, miR-18a, miR-192, miR-429, miR-618, miR-95, miR-130a, miR-152, miR-194, miR-27b, miR-301, miR-326, miR-345, miR-361, miR-422a, miR-579, miR-642, miR-99a, miR-520D-3p and miR-629.

For the avoidance of doubt, it will be understood that "the at least one miRNA is selected from a group of miRNAs", as used herein, means that the method in question, whether carried out for a diagnostic, prognostic, or therapeutic purpose, can be carried out with any one of the listed miRNAs or with any plurality of the listed miRNAs (e.g., two, three, four, or more of the listed miRNAs). It follows that any one or more of the listed miRNAs may be explicitly excluded. For example, where the at least one miRNA is selected from the group consisting of miR-505, miR-203, miR-654-3p, miR-655, miR-184, miR-301b, miR-425-5p, miR-502, miR-21, miR-let-7g and miR-335, the method may include detecting and/or assessing the level of any combination of miR-505, miR-203, miR-654-3p, miR-655, miR-184, miR-301b, miR-425-5p, miR-502, miR-21, and miR-let-7g to the exclusion of miR-335.

According to an aspect of the invention, there is provided a method of diagnosing and/or monitoring traumatic brain injury (TBI) in a subject, the method comprising determining a level of at least two miRNAs in a sample from the subject, wherein the miRNA is selected from the group consisting of miR-27b-3p, let-7i-5p, miR-142-3p, miR-107 and miR-135b-5p.

According to an aspect of the invention, there is provided a method of diagnosing and/or monitoring traumatic brain injury (TBI) in a subject, the method comprising determining a level of at least one miRNA in a sample from the subject, wherein the miRNA is selected from the group consisting of: miR-425-5p; miR-502; miR-21; and miR-335.

Traumatic brain injury occurs when an external force traumatically injures the brain. There are different systems for classifying TBI based on, for example, severity, type of injury and prognosis. The most commonly used system for classifying TBI is the Glasgow Coma Scale (GCS), which grades a person's level of consciousness on a scale of 3-15 based on verbal, motor, and eye-opening reactions to stimuli. In general, a TBI with a GCS score of 13 or above is defined as mild, 9-12 as moderate and 8 or below as severe. Another system, the Mayo Classification System, has three main classifications including definite moderate-severe TBI, probable mild TBI, and possible TBI. Multiple criteria are used in each diagnosis including loss of consciousness, post-traumatic amnesia, skull fracture, and evidence of neuroradiological abnormalities including subdural haematoma, cerebral contusion, and hemorrhagic contusion. The classification of TBI using the GCS or Mayo systems will be known to those skilled in the art.

As used herein, references to "mild", "moderate" and "severe" TBI are made in accordance with the GCS. References herein to "moderate-to-severe" TBI encompass both moderate and severe TBI in accordance with the GCS.

As used herein, a reference to mild TBI (mTBI) is also a reference to concussion.

The diagnosis and/or monitoring of TBI using the biomarkers of the present invention is expected to support clinical decision making and treatment regimens in a variety of contexts, including the following situations: as part of the initial assessment by paramedics to determine whether patients should be transported to a facility with neurosurgical expertise, a major trauma centre or a local trauma unit; in the emergency department of hospitals to determine appropriate treatment, including the need for a CT brain scan; pitch-side, to assist decision making as to the removal of a player from play and assessment of the need to take a player to hospital; in sports clinics, to confirm a concussive event and enable decision making with regard to returning to play; in combat situations, to determine the need to dispatch a rescue team and evacuate a victim. Thus, subjects for whom the present invention provides particular benefit include accident victims, sports players and military personnel.

In any case, but perhaps particularly where the subject is at greater risk for a TBI (e.g., where the subject is a professional athlete or enlisted in the military), a sample may be obtained from the subject at a time prior to any known or recent trauma (e.g., near the beginning of a sporting career or prior to a military deployment) and any miRNAs of interest can be assessed at that time or later, when the subject has experienced a possible TBI. Such samples may thereby provide an internal reference standard.

In some embodiments, the subject is human.

The TBI may be mild TBI (mTBI), moderate TBI or severe TBI (sTBI). In some embodiments, the TBI is moderate-to-severe TBI (m-sTBI).

The level of the miRNA or of each miRNA in the sample may be determined quantitatively or semi-quantitatively. By "quantitatively", it will be understood that the absolute amount or concentration of the miRNA or of each miRNA in the sample is determined. The absolute amount of the miRNA or of each miRNA in the sample can then be compared to a predetermined threshold (e.g. a published literature value for expected normal levels), a known level of the same or a reference miRNA in a control sample taken from a healthy subject, or the amount of a reference miRNA in the sample taken from the subject. In some embodiments, the subject is diagnosed as having a TBI when the level of the miRNA is below the predetermined threshold, or decreased relative to a reference or control sample. In other embodiments, the subject is diagnosed as having a TBI when the level of the miRNA is increased compared to the predetermined threshold.

By "semi-quantitatively", it will be understood that the level of the or each miRNA of interest is measured relative to a reference.

The reference may be an invariant miRNA, i.e. a miRNA having an expression level that remains substantially unchanged between healthy subjects and those having a TBI. A subject may be diagnosed as suffering from a TBI if the level of the miRNA or of each miRNA of interest is increased or decreased relative to that of an invariant miRNA. Suitable invariant miRNAs include miR-331, miR-223*, miR-23a-3p and miR148b-3p.

miR-23a-3p and miR148b-3p are invariant in saliva only.

In some embodiments, the level of the miRNA or of each miRNA in the sample obtained from the subject may be about 0.01 times to about 100 times, about 0.05 times to about 50 times, about 0.1 times to about 10 times, about 0.5 times to about 5 times, about 1.0 to about 3 times, or about 1.5 times to about 2.0 times lower or higher than the level in the control sample, the reference level or the published value.

Where a device or method is employed to generate a value, we may qualify that value with the term "about" in order to capture the stated value and any variation of that value inherent to the device or method employed. Where values or ranges of values are specifically disclosed, "about" may mean plus-or-minus 10% of the stated value or range. For example, about 10 minutes may mean 9-11 minutes.

The level of the miRNA or of each miRNA of interest can be determined using methods known to those skilled in the art. In some embodiments, determining the level of the miRNA or of each miRNA of interest comprises amplifying the miRNA. In some embodiments, total miRNA may be first isolated from the sample using standard techniques, for example using the miRNeasy mini kit (Qiagen). The amount of the miRNA of interest can then be determined. In some embodiments, the level of the miRNA or of each miRNA of interest in the sample is determined using PCR (polymerase chain reaction). For example, quantitative PCR may be used for quantitative determination of the level of the miRNA or of each miRNA of interest. PCR may also be used for semi-quantitative determination, by comparing the level of the miRNA or of each miRNA of interest in the sample with that of a reference (e.g. an invariant miRNA).

Suitable techniques for miRNA detection and/or quantification, which will be known to those skilled in the art, include qPCR, miRNA assays, next-generation sequencing (NGS), and multiplex miRNA profiling assays.

In some embodiments, the level of the miRNA or of each miRNA of interest is determined using in-situ hybridization, for example using a probe (e.g., a labelled probe) specific for the miRNA.

The level of miRNA may be determined in a sample which was obtained from the subject immediately after injury (i.e. less than 1 hour after injury), and/or in a sample obtained at one or more time points a few hours or days after injury. Thus, changes in the miRNA level can be detected over time to enable monitoring of a TBI. In the event miRNA levels change over time, the methods described herein for monitoring TBI can be expanded to include maintaining or adjusting the subject's treatment regimen accordingly.

Depending on the specific miRNA and the type of TBI, the level of miRNA in the subject may change significantly over time. In some embodiments, it may therefore be advantageous to measure the miRNA relatively soon after injury to enable an accurate diagnosis. In some embodiments, the level of miRNA is determined in a sample obtained from the subject no more than 72 hours, no more than 48 hours, no more than 36 hours, no more than 24 hours, no more than 12 hours, no more than 6 hours, no more than 4 hours, no more than 2 hours or no more than 1 hour after injury.

The level of some miRNAs is substantially stable over time, thus allowing a diagnosis to be made a few hours, days or even weeks after injury. In some embodiments, the level of miRNA is determined in a sample obtained from the subject up to 20, 18, 15, 12, 10, 8, 5 or 2 days from injury.

In some embodiments, the level of miRNA is determined in a sample obtained from the subject immediately after injury (e.g. at T=0 h), at 4-12 hours after injury, at 48-72 hours after injury, or at 15 days after injury.

In some embodiments, the level of miRNA is determined in a sample obtained from the subject at least 24 hours after injury. In some embodiments, the level of miRNA is determined in a sample obtained from the subject 15 days or fewer after injury. In some embodiments, the level of miRNA is determined in a sample obtained from the subject between 24 hours and 15 days after injury, or between 24 hours and 10 days after injury, or between 24 hours and 7 days after injury, or between 48 hours and 5 days after injury.

In some embodiments, the TBI is mild TBI (mTBI) or moderate-to-severe TBI (m-sTBI) and the at least one miRNA is selected from the group consisting of miR-505, miR-203, miR-654-3p, miR-655, miR-184, miR-301b, miR-425-5p, miR-502, miR-21, miR-let-7g, miR-335, hsa-miR-126*, miR-193a-5p, miR-144*, miR-190, miR-194, miR-365, miR-590-3p, miR-624, miR-625*, and miR-671-3p.

In some embodiments, the TBI is mild TBI (mTBI) and the miRNA is selected from the group consisting of miR-425-5p and miR-502. The subject may be diagnosed as having mTBI if the level of miR-425-5p and/or miR-502 is determined to be below a predetermined threshold, or is decreased relative to a reference.

In some embodiments, a level of miR-425-5p and/or miR-502 which is below a predetermined threshold, or decreased relative to a reference, is diagnostic of mTBI when the level is determined in a sample obtained less than 48 hours after injury.

In some embodiments, the TBI is moderate-to-severe TBI (m-sTBI) and the miRNA is selected from the group consisting of miR-21 and miR-335. The subject may be diagnosed as having moderate-to-severe TBI if the level of miR-21 and/or miR-335 is determined to be above a predetermined threshold, or increased relative to a reference.

In some embodiments, a level of miR-21 and/or miR-335 which is above a predetermined threshold, or increased relative to a reference, is diagnostic of moderate-to-severe TBI when the level is determined in a sample obtained up to 15 days after injury.

In some embodiments, the TBI is moderate-to-severe TBI (m-sTBI) and the at least one miRNA is selected from the group consisting of miR-10a, miR-132, miR-223, miR-143, miR-148b, miR-18a, miR-192, miR-429, miR-618, miR-95, miR-130a, miR-152, miR-194, miR-27b, miR-301, miR-326, miR-345, miR-361, miR-422a, miR-579, miR-642, miR-99a, miR-520D-3p and miR-629.

The subject may be diagnosed as having m-sTBI if the level of miR-10a, miR-132, miR-223, miR-143, miR-148b, miR-18a, miR-618, miR-95, miR-130a, miR-152, miR-194, miR-27b, miR-301, miR-326, miR-345, miR-361, miR-422a, miR-579, miR-642 and/or miR-99a is determined to be above a predetermined threshold, or is increased relative to a reference.

The subject may be diagnosed as having m-sTBI if the level of miR-192, miR-429, miR-520D-3p and/or miR-629 is determined to be below a predetermined threshold, or is decreased relative to a reference.

The miRNAs may be used individually to diagnose TBI. For example, in sport concussion, miR-502 or miR-425-5p could be used to confirm that a traumatic brain injury has occurred.

Thus, a further aspect of the present invention is a method of determining the severity of TBI, and the steps of this method can be repeated to monitor the subject over time. It will be appreciated that a positive result for a single miRNA (e.g. the level of a single miRNA is determined to be above/below a predetermined threshold, or is increased/decreased relative to a reference) is sufficient to determine the severity of TBI. For example, if the level of miR-425-5p is below a predetermined threshold, or decreased relative to a reference, the severity of the TBI is determined to be mild (mTBI). However, it may be convenient to combine different miRNAs (e.g. in a test panel) to facilitate the assessment of TBI severity.

In some embodiments, the method comprises determining a level of a plurality (e.g., two or more) miRNAs in the sample. In some embodiments the two or more miRNAs are selected from the group consisting of: miR-425-5p; miR-502; miR-21; and miR-335.

In some embodiments, the method comprises determining the level of:
(i) a first miRNA selected from miR-425-5p and miR-502; and
(ii) a second miRNA selected from miR-21 and miR-335.

A subject may be diagnosed as having a TBI if the level of miR-425-5p or miR-502 is determined to be below a predetermined threshold, or is decreased relative to a reference, or the level of miR-21 or miR-335 is determined to be above a predetermined threshold, or increased relative to a reference.

In some embodiments, the TBI is mild TBI (mTBI) and the at least one miRNA is selected from the group consisting of let-7c-5p, let-7i-5p, miR-142-3p, miR-148a-3p, miR-15b-5p, miR-16-5p, miR-181a-5p, miR-20a-5p, miR-20b-5p, miR-221-3p, miRmmiR-29a-3p, miR-29c-3p, miR-424-5p, miR-30a-5p, miR-107, miR-135b-5p, miR-199b-5p, miR-324-5p, and miR-652-3p, or a combination thereof. The subject may be diagnosed as having mTBI if there is a fold change of at least 0.5, at least 1.0, at least 1.5, at least 2.0, at least 2.5, at least 3.0, at least 3.5 or at least 4.0 in level of the microRNA compared to a reference. In some embodiments, the subject is diagnosed as having mTBI if the level(s) of the microRNA(s) is/are increased compared to a reference.

In some embodiments, the TBI is mTBI or concussion and the at least one miRNA is selected from the group consisting of miR-27b-3p, let-7i-5p, miR-142-3p, miR-107 and miR-135b-5p, or any combination thereof. In embodiments an upregulated level of the at least one miRNA, an increase above a predetermined threshold or an increase relative to a control is indicative of mTBI or concussion.

The sequences and accession numbers for miRNAs described herein are provided in Table 1:

TABLE 1

| miRNA | sequence | miRBase Accession no. |
| --- | --- | --- |
| hsa-miR-21 | uagcuuaucagacugauguuga (SEQ ID No. 1) | MIMAT0000076 |
| hsa-miR-425-5p | aaugacacgaucacucccguuga (SEQ ID No. 2) | MIMAT0003393 |
| hsa-miR-502-5p (also known as hsa-miR-502) | auccuugcuaucugggugcua (SEQ ID No. 3) | MIMAT0002873 |
| hsa-miR-335-5p (also known as hsa-miR-335) | ucaagagcaauaacgaaaaaugu (SEQ ID No. 4) | MIMAT0000765 |
| hsa-miR-301b-3p (also known as hsa-miR-301b) | cagugcaaugauauugucaaagc (SEQ ID No. 5) | MIMAT0004958 |

TABLE 1-continued

| miRNA | sequence | miRBase Accession no. |
|---|---|---|
| hsa-miR-184 | uggacggagaacugauaaggu (SEQ ID No. 6) | MIMAT0000454 |
| hsa-miR-505-3p (also known as hsa-miR-505) | cgucaacacuugcugguuuccu (SEQ ID No. 7) | MIMAT0002876 |
| hsa-miR-203a-3p (also known as hsa-miR-203a, hsa-miR-203) | gugaaauguuuaggaccacuag (SEQ ID No. 8) | MIMAT0000264 |
| hsa-miR-654-3p | uaugucugcugaccaucaccuu (SEQ ID No. 9) | MIMAT0004814 |
| hsa-miR-655-3p (also known as hsa-miR-655) | auaauacaugguuaaccucuuu (SEQ ID No. 10) | MIMAT0003331 |
| hsa-miR-331-3p (also known as hsa-miR-331) | gccccuggggccuauccuagaa (SEQ ID No. 11) | MIMAT0000760 |
| hsa-miR-223-5p (also known as hsa-miR-223*) | cguguauuugacaagcugaguu (SEQ ID No. 12) | MIMAT0004570 |
| hsa-miR-let-7g | ugagguaguaguuuguacaguu (SEQ ID No. 13) | MIMAT0000414 |
| hsa-miR-126* (also known as hsa-miR-126-5p) | cauuauuacuuuugguacgcg (SEQ ID No. 14) | MIMAT0000444 |
| hsa-miR-193a-5p | ugggucuuugcgggcgagauga (SEQ ID No. 15) | MIMAT0004614 |
| hsa-miR-144* (also known as hsa-miR-144-5p) | ggauaucaucauauacuguaag (SEQ ID No. 16) | MIMAT0004600 |
| hsa-miR-190 (also known as hsa-miR-190a or hsa-miR-190a-3p) | cuauauaucaaacauauuccu (SEQ ID No. 17) | MIMAT0026482 |
| hsa-miR-194 (also known as hsa-miR-194-5p) | uguaacagcaacuccaugugga (SEQ ID No. 18) | MIMAT0000460 |
| hsa-miR-365 (also known as hsa-miR-365a-3p) | uaaugccccuaaaaauccuuau (SEQ ID No. 19) | MIMAT0000710 |
| hsa-miR-590-3p (also known as hsa-miR-590) | uaauuuuauguauaagcuagu (SEQ ID No. 20) | MIMAT0004801 |
| hsa-miR-624 | uaguaccaguaccuuguguuca (SEQ ID No. 21) | MI0003638 |
| hsa-miR-625* (also known as hsa-miR-625-3p) | gacuauagaacuuuccccuca (SEQ ID No. 22) | MIMAT0004808 |
| hsa-miR-671-3p | uccgguucucagggcuccacc (SEQ ID No. 23) | MIMAT0004819 |
| hsa-let-7c-5p | ugagguaguagguuguauggu (SEQ ID No. 24) | MIMAT0000064 |
| hsa-let-7i-5p (also known as hsa-let-7i) | ugagguaguaguuugugcuguu (SEQ ID No. 25) | MIMAT0000415 |
| hsa-miR-142-3p | uguaguguuuccuacuuuaugga (SEQ ID No. 26) | MIMAT0000434 |
| hsa-miR-148a-3p (also known as hsa-miR-148a) | ucagugcacuacagaacuuugu (SEQ ID No. 27) | MIMAT0000243 |
| hsa-miR-15b-5p (also known as hsa-miR-15b) | uagcagcacaucaugguuuaca (SEQ ID No. 28) | MIMAT0000417 |
| hsa-miR-16-5p (also known as hsa-miR-16) | uagcagcacguaaauauuggcg (SEQ ID No. 29) | MIMAT0000069 |
| hsa-miR-181a-5p (also known as hsa-miR-181a) | aacauucaacgcugucggugagu (SEQ ID No. 30) | MIMAT0000256 |
| hsa-miR-20a-5p (also known as hsa-miR-20; hsa-miR-20a) | uaaagugcuuauagugcagguag (SEQ ID No. 31) | MIMAT0000075 |
| hsa-miR-20b-5p (also known as hsa-miR-20b) | caaagugcucauagugcagguag (SEQ ID No. 32) | MIMAT0001413 |

TABLE 1-continued

| miRNA | sequence | miRBase Accession no. |
|---|---|---|
| hsa-miR-221-3p (also known as hsa-miR-221) | agcuacauugucugcuggguuuc (SEQ ID No. 33) | MIMAT0000278 |
| hsa-miR-24-3p (also known as hsa-miR-24) | uggcucaguucagcaggaacag (SEQ ID No. 34) | MIMAT0000080 |
| hsa-miR-27b-3p (also known as hsa-miR-27b) | uucacaguggcuaaguucugc (SEQ ID No. 35) | MIMAT0000419 |
| hsa-miR-29a-3p (also known as hsa-miR-29a) | uagcaccaucugaaaucgguua (SEQ ID No. 36) | MIMAT0000086 |
| hsa-miR-29c-3p (also known as hsa-miR-29c) | uagcaccauuugaaaucgguua (SEQ ID No. 37) | MIMAT0000681 |
| hsa-miR-30a-5p (also known as hsa-miR-30a) | uguaaacauccucgacuggaag (SEQ ID No. 38) | MIMAT0000087 |
| hsa-miR-107 (also known as hsa-miR-107-10) | agcagcauuguacagggcuauca (SEQ ID No. 39) | MI0000114 |
| hsa-miR-135b-5p (also known as hsa-miR-135b) | uauggcuuuucauuccuauguga (SEQ ID No. 40) | MIMAT0000758 |
| hsa-miR-199b-5p (also known as hsa-miR-199b) | cccaguguuuagacuaucuguuc (SEQ ID No. 41) | MIMAT0000263 |
| hsa-miR-324-5p | cgcaucccuagggcauuggugu (SEQ ID No. 42) | MIMAT0000761 |
| hsa-miR-652-3p (also known as hsa-miR-652) | aauggcgccacuagggguugug (SEQ ID No. 43) | MIMAT0003322 |
| hsa-miR-424-5p (also known as hsa-miR-424) | cagcagcaauucauguuuugaa (SEQ ID No. 44) | MIMAT0001341 |
| hsa-miR-10a (also known as hsa-miR-10-5p) | uacccuguagauccgaauuugug (SEQ ID No. 45) | MIMAT0000253 |
| hsa-miR-132 (also known as hsa-miR-132-3p) | uaacagucuacagccauggucg (SEQ ID No. 46) | MIMAT0000426 |
| hsa-miR-223 (also known as hsa-miR-223-3p) | ugucaguuugucaaauacccca (SEQ ID No. 47) | MIMAT0000280 |
| hsa-miR-143 (also known as hsa-miR-143-3p) | ugagaugaagcacuguagcuc (SEQ ID No. 48) | MIMAT0000435 |
| hsa-miR-148b (also known as hsa-miR-148b-3p) | ucagugcaucacagaacuuugu (SEQ ID No. 49) | MIMAT0000759 |
| hsa-miR-18a (also known as hsa-miR-18; hsa-miR-18a-5p) | uaaggugcaucuagugcagauag (SEQ ID No. 50) | MIMAT0000072 |
| hsa-miR-192 (also known as hsa-miR-192-5p) | cugaccuaugaauugacagcc (SEQ ID No. 51) | MIMAT0000222 |
| hsa-miR-429 | uaauacugucugguaaaaccgu (SEQ ID No. 52) | MIMAT0001536 |
| hsa-miR-618 | aaacucuacuugaccuucugagu (SEQ ID No. 53) | MIMAT0003287 |
| hsa-miR-95 (also known as hsa-miR-95-5p) | ucaauaaaugucuguugaauu (SEQ ID No. 54) | MIMAT0026473 |
| hsa-miR-130a (also known as hsa-miR-130a-3p) | cagugcaauguuaaagggcau (SEQ ID No. 55) | MIMAT0000425 |
| hsa-miR-152 (also known as hsa-miR-152-5p) | agguucugugauacacuccgacu (SEQ ID No. 56) | MIMAT0026479 |
| hsa-miR-27b (also known as hsa-miR-27b-3p) | uucacaguggcuaaguucugc (SEQ ID No. 57) | MIMAT0000419 |
| hsa-miR-301 (also known as hsa-miR-301a-3p or hsa-miR-301a) | cagugcaauaguauugucaaagc (SEQ ID No. 58) | MIMAT0000688 |

TABLE 1-continued

| miRNA | sequence | miRBase Accession no. |
|---|---|---|
| hsa-miR-326 | ccucugggcccuuccuccag (SEQ ID No. 59) | MIMAT0000756 |
| hsa-miR-345 (also known as hsa-miR-345-5p) | gcugacuccuaguccagggcuc (SEQ ID No. 60) | MIMAT0000772 |
| hsa-miR-361 (also known as hsa-miR-361-5p) | uuaucagaaucuccagggguac (SEQ ID No. 61) | MIMAT0000703 |
| hsa-miR-422a | acuggacuuagggucagaaggc (SEQ ID No. 62) | MIMAT0001339 |
| hsa-miR-579 (also known as hsa-miR-579-3p) | uucauuugguauaaaccgcgauu (SEQ ID No. 63) | MIMAT0003244 |
| hsa-miR-642 (also known as hsa-miR-642a-5p; hsa-miR-642) | gucccucuccaaaugugucuug (SEQ ID No. 64) | MIMAT0003312 |
| hsa-miR-99a (also known as hsa-miR-99a-5p) | aacccguagauccgaucuugug (SEQ ID No. 65) | MIMAT0000097 |
| hsa-miR-520D-3p (also know as hsa-miR-520D) | aaagugcuucucuuuggugggu (SEQ ID No. 66) | MIMAT0002856 |
| hsa-miR-629 (also known as hsa-miR-629-5p) | uggguuuacguugggagaacu (SEQ ID No. 67) | MIMAT0004810 |
| hsa-miR-23a-3p (also known as hsa-miR-23a) | aucacauugccagggauuucc (SEQ ID No. 68) | MIMAT0000078 |
| hsa-miR-148b-3p (also known as hsa-miR-148b) | ucagugcaucacagaacuuugu (SEQ ID No. 69) | MIMAT0000759 |

Conveniently the sample may be any appropriate fluid or tissue sample obtained from the subject. For example, the biological sample may comprise at least one of the group consisting of: urine, saliva, whole blood, plasma, serum, sputum, semen, faeces, a nasal swab, tears, a vaginal swab, a rectal swab, a cervical smear, a tissue biopsy, and a urethral swab. In some embodiments the sample is a fluid sample. Suitably, the sample is one that can be readily obtained from the individual, such as urine, saliva, blood and sputum. In some embodiments, the sample comprises saliva, blood, plasma or serum. It will be appreciated that in some embodiments the process of obtaining the sample does not form part of the invention described herein.

In some embodiments, the sample comprises or is constituted by serum. Not only does serum have practical advantages, but it is also free of anticoagulants such as heparin, a potential inhibitor of PCR reactions. Serum may also be less affected by haemolysis, compared to plasma.

In some embodiments, the sample is saliva. Saliva can be easily obtained from the patient (e.g. pitch-side, or in the field), without specialist training or medical equipment.

miRNAs which have been found to be indicative of mTBI in saliva include: hsa-let-7ca-5p, hsa-let-7i-5p, hsa-miR-1421-3p, hsa-miR-148a-3p, hsa-miR-15b-5p, hsa-miR-16-5p, hsa-miR-181a-5p, hsa-miR-20a-5p, hsa-miR-20b-5p, hsa-miR-221-3p, hsa-miR-24-3p, hsa-miR-27b-3p, hsa-miR-29a-3p, hsa-miR-29c-3p, hsa-miR-340-5p, hsa-miR-424-5p; miR-30a-5p; miR-107; miR-135b-5p; miR-199b is selected from the group consisting of -5p; miR-324-5p; and miR-652-3p.

miRNAs which have been found to be indicative of mTBI in saliva include: miR-27b-3p, let-7i-5p, miR-142-3p, miR-107 and miR-135b-5p.

The present invention provides a method of diagnosing and/or monitoring mild traumatic brain injury (mTBI) in a subject, the method comprising determining a level of at least one miRNA in a saliva sample obtained from the subject, wherein the at least one miRNA is selected from the group consisting of miR-27b-3p, let-7i-5p, miR-142-3p, miR-107 and miR-135b-5p, or any combination thereof.

Optionally the at least one miRNA is miR-27b-3p. Alternatively the at least one miRNA is let-7i-5p. Conveniently, the at least one miRNA is miR-142-3p. In embodiments the at least one miRNA is miR-107. In other embodiments the at least one miRNA is miR-135b-5p.

In embodiments, an upregulated level in saliva of the at least one miRNA selected from the group consisting of miR-27b-3p, let-7i-5p, miR-142-3p, miR-107 and miR-135b-5p is indicative of mTBI or concussion. In embodiments, the subject is diagnosed as having mTBI if the level of the at least one miRNA is above a predetermined threshold or increased relative to a control.

An upregulated level indicative of mTBI can be equivalent to a fold change of 2.0 or more obtained via the 2-ΔΔCT method. In embodiments an upregulated level indicative of mTBI can be equivalent to a fold change of 2.0 or more obtained via the 2-ΔΔCT method for at least one miRNA selected from the group consisting of miR-27b-3p, let-7i-5p, miR-142-3p, miR-107 and miR-135b-5p.

The method of diagnosing and/or monitoring mTBI in a subject can comprise contacting a saliva sample obtained from the subject with at least one miRNA-specific oligonucleotide probe having at least 70% identity to the complement of a sequence selected from SEQ ID Nos: 25, 26, 35, 39 or 40.

The method can further comprise quantifying the at least one miRNA-specific oligonucleotide probe and comparing said expression level to a reference miRNA or a control expression level obtained or derived from a healthy subject.

A 1.5 fold or greater difference, such as a 2.0 fold or greater difference, between the subject and the control is indicative of mTBI.

The methods of the present invention may comprise determining a level of at least a second miRNA in the saliva sample obtained from the subject.

The methods of the present invention may comprise determining a level of at least two miRNAs in the saliva sample obtained from the subject. In embodiments a first of the at least two miRNAs are selected from the group consisting of miR-27b-3p, let-7i-5p, miR-142-3p, miR-107 and miR-135b-5p. In embodiments the at least two miRNAs are selected from the group consisting of miR-27b-3p, let-7i-5p, miR-142-3p, miR-107 and miR-135b-5p.

Optionally, the at least two miRNAs are let-7i-5p and miR-142-3p.

Alternatively the at least two miRNAs are let-7i-5p and miR-27b-3p.

Conveniently the at least two miRNAs are let-7i-5p and miR-107.

In embodiments the at least two miRNAs are let-7i-miR-135b-5p.

In further embodiments the at least two miRNAs are miR-142-3p and miR-27b-3p. Optionally, the at least two miRNAs are miR-142-3p and miR-107.

Alternatively the at least two miRNAs are miR-142-3p and miR-135b-5p.

Conveniently the at least two miRNAs are miR-27b-3p and miR-107.

In embodiments the at least two miRNAs are miR27b-3p and miR-135b-5p.

In further embodiments the at least two miRNAs are miR-107 and miR-135b-5p.

In embodiments the method includes determining a level of the miRNAs miR-27b-3p, let-7i-5p, miR-142-3p, miR-107 and miR-135b-5p.

In embodiments the method further comprises determining a level of one or more additional miRNAs selected from the group consisting of let-7c-5p, let-7i-5p, miR-142-3p, miR-148a-3p, miR-15b-5p, miR-16-5p, miR-181a-5p, miR-20a-5p, miR-20b-5p, miR-221-3p, miR-24-3p, miR-27b-3p, miR-29a-3p, miR-29c-3p, and miR-424-5p, miR-30a-5p, miR-107, miR-135b-5p, miR-199b-5p, miR-324-5p and miR-652-3p.

An upregulated level of two or more miRNAs indicative of mTBI can be equivalent to a fold change of 1.5 or more, or 2.0 or more, for example obtained via the 2-ΔΔCT method (also referred to as the 'double delta Ct method' or the '2 delta Ct method' where the method of detection is a quantitative polymerase chain reaction ("PCR") based method.

In embodiments, the level of miRNA is determined in a saliva sample obtained from the subject at least 24 hours after injury. In some embodiments, the level of miRNA is determined in a saliva sample obtained from the subject 15 days or fewer after injury. In some embodiments, the level of miRNA is determined in a saliva sample obtained from the subject between 24 hours and 15 days after injury, or between 24 hours and 10 days after injury, or between 24 hours and 7 days after injury, or between 48 hours and 5 days after injury.

Levels of miRNAs may be used to track recovery of a subject from injury. Thus, the present invention encompasses monitoring the recovery of a subject from TBI, as an alternative or in addition to the initial diagnosis.

In some embodiments, the method comprises monitoring TBI and the level of the at least one miRNA is determined in a sample obtained from the subject at least 2, at least 3, at least 5, at least 7, at least 10 or at least 14 days after injury. In some embodiments, the level of the at least one miRNA is determined in a sample obtained from the subject 15 days after injury. In some embodiments, the level of the at least one miRNA is determined in at least two samples obtained at different time intervals after injury, thus allowing recovery to be monitored. For example, miRNA levels could be determined at 7 and 14 days following injury, or at 5, 10 and 15 days following injury. A return of miRNA levels to normal may be indicative of recovery of the subject from the TBI.

In some embodiments, a subject is determined to have recovered from mTBI if the level of miR-425-5p and/or miR-502 is no longer below a predetermined threshold or no longer decreased relative to a reference.

In some embodiments, a subject is determined to have recovered from moderate-to-severe TBI if the level of miR-21 and/or miR-335 is no longer above a predetermined threshold or no longer increased relative to a reference.

The diagnosis of a subject as suffering from a TBI, and in particular diagnosis of mild TBI or moderate-to-severe TBI, may facilitate in the determination of an appropriate treatment. The present invention thus provides a test that enables healthcare workers, such as physicians, clinicians, paramedics, and even non-medical personnel (e.g. teachers, sports coaches, military personnel) to decide on appropriate action for a subject suspected of having a TBI. A subject determined as having a TBI may therefore receive the most appropriate treatment as a result of a diagnosis being made. The method of the invention may thus further comprise directing appropriate therapy to a subject diagnosed with a TBI.

A subject diagnosed with TBI may be further evaluated, e.g. by CT scanning. In some embodiments, the subject is admitted to hospital. In some embodiments, if moderate-to-severe TBI can be ruled out, the subject may not need to be admitted to hospital for evaluation. A subject diagnosed with moderate-to-severe TBI may be admitted to hospital, or a specialist centre with neurotrauma expertise.

A subject diagnosed with a TBI (particularly mTBI) outside a hospital environment, for example, at a sporting event, during combat or during play, may be removed from play or combat immediately. The subject may subsequently be started on a graduated return to play or combat.

In a further aspect, there is provided a method for determining whether it is appropriate to administer to a subject a therapy for alleviating TBI, the method comprising: determining a level of at least one miRNA in a sample from the subject; and determining whether or not it is appropriate to administer a therapy for alleviating TBI, based on the level of the at least one miRNA.

It will be appreciated that the step of administering the therapy to the subject does not form a part of the claimed method, unless specifically stated.

In some embodiments the method may further comprise administering to the subject an appropriate treatment. In some embodiments, the treatment may comprise a therapy for alleviating TBI. Accordingly, the invention features methods of diagnosing and treating TBI in a subject, the method comprising the steps of (a) obtaining a sample (e.g., a sample of blood, plasma, urine, or saliva) from the subject; (b) detecting one or more miRNAs (selected from those described herein); diagnosing the patient as having a TBI when the level(s) of the miRNA(s) differ from a reference standard (as described herein); and administering a treatment for the TBI.

In a further aspect, the invention provides a method of determining an appropriate treatment to a subject suspected of suffering from a TBI, the method comprising identifying whether or not the subject has a TBI by determining a level of at least one miRNA in a sample from the subject.

If a subject is identified as having a TBI, an appropriate treatment may include one or more of the following: further evaluating the subject, for example by further tests (e.g. verbal, cognitive, motor and/or optical tests), CT and/or MII scanning; removing the subject from activity (e.g. the activity during which the TBI was incurred); admitting the subject to hospital or a specialist clinic; surgery; and administering a therapy for alleviating TBI to the subject.

The therapy for alleviating TBI may include neuroprotective drugs, e.g. drugs to treat cerebral swelling such as mannitol and hypertonic saline, and/or other neuroprotective measures, such as avoidance of hypertensive resuscitation and the use of sedation.

In some embodiments, the subject may be subsequently monitored to track their recovery, for example in a hospital or clinic setting.

According to a further aspect of the invention, there is provided a method of detecting and/or determining a level of a target miRNA in a subject, the method comprising the steps of (a) obtaining a sample from the subject; and (b) detecting and/or determining the level of the target miRNA in the sample by contacting the sample with a probe that is specific for the target miRNA.

The sample may be any appropriate fluid or tissue sample obtained from the subject, as defined above. In some embodiments, the sample is blood, serum, plasma, urine or saliva.

In some embodiments, the method may comprise determining the level of two or more target miRNAs in the sample.

According to a further aspect of the invention, there is provided a therapy for alleviating TBI for use in a method of treating a subject in need thereof, wherein said subject is identified as having a TBI by determining a level of at least one miRNA in a sample from the subject.

The step of determining the level of the target miRNA may comprise contacting the sample with a substrate functionalized with the probe, for example a chip comprising the probe. The substrate or chip may conveniently include multiple probes, each specific for a different target miRNA.

The subject may have suffered an injury, in particular a head injury. The subject may be suspected as having a TBI. The subject may be suspected of having mTBI or concussion. In some embodiments, the sample is obtained no more than 72 hours, no more than 48 hours, no more than 36 hours, no more than 24 hours, no more than 12 hours, no more than 6 hours, no more than 4 hours, no more than 2 hours or no more than 1 hour after injury. In some embodiments the sample is obtained 24 hours or more after the injury. In further embodiments the sample is obtained from the subject 15 days or fewer after injury. In some embodiments the sample is obtained from the subject between 24 hours and 15 days after injury, or between 24 hours and 10 days after injury, or between 24 hours and 7 days after injury, or between 48 hours and 5 days after injury.

In some embodiments, the method further comprises treating the subject. The treatment may include one or more of the following: further evaluating the subject, for example by further tests (e.g. verbal, cognitive, motor and/or optical tests), CT and/or MRI scanning; removing the subject from activity (e.g. the activity during which the TBI was incurred); admitting the subject to hospital or a specialist clinic; and administering a therapy for alleviating TBI to the subject. In some embodiments, the treatment comprises administering an effective amount of a neuroprotective drug.

Thus, in yet a further aspect the invention provides a method of treating TBI, the method comprising:

determining a level of at least one miRNA in a sample from the subject; and if the level of the at least one miRNA is indicative of mTBI, administering a treatment appropriate for mTBI; or if the level of the at least one miRNA is indicative of m-sTBI, administering a treatment appropriate for m-sTBI.

It will be appreciated by those skilled in the art that different treatment pathways may be used for mTBI and m-sTBI.

In yet a further aspect the invention provides a method of treating a subject with suspected mTBI, the method comprising:

i) determining whether an upregulated level of at least one miRNA selected from the group consisting of miR-27b-3p, let-7i-5p, miR-142-3p, miR-107 and miR-135b-5p is detectable in a saliva sample obtained from the subject, and ii) if an upregulated level of at least one miRNA is detected providing a treatment for mTBI to the subject.

A subject with mTBI may be treated as follows:

An athlete diagnosed with mTBI would typically be started on a graduated return to play protocol (as defined by the Berlin Consensus Conference on Concussion and individual sport authorities, e.g. RFU). This would involve a period of rest followed by a gradual increase in level of exertion and exposure to contact. An athlete with mTBI would typically not be able to play for a period that varies between 6 and 23 days, depending on level of medical supervision and age. Conversely, if mTBI was excluded, the athlete would not have any restrictions and could train as normal the following day. If diagnosed in a pre-hospital setting, mTBI would be an indication for a patient to seek medical attention (e.g. in hospital or in primary care), whereas, if mTBI was excluded no medical review would be indicated.

A person with mTBI must not be left unsupervised for 24-48 hours and must not drive or operate a fork lift or open machinery until recovered.

Military personnel diagnosed with mTBI would be removed from the operational theatre and would be rested, whereas, if mTBI could be excluded, that person would continue on active duties.

In the NHS, a person with mTBI may be kept in hospital for observation or may have a CT scan according to the guidance issued by NICE, whereas if mTBI could be excluded, that patient could be discharged straightaway.

A person diagnosed with mTBI would typically be asked not to return to work or study for a certain period of time.

A person diagnosed with mTBI may be referred to a mild TBI clinic or a neurology clinic or a neurosurgery clinic. Typical interventions for mTBI consist of education, advice in regard to work, study and driving, medical management of typical sequelae such as headache or anxiety or mood disorder or post-traumatic stress disorder with medication and/or psychological intervention if necessary, and referral to other services as indicated, e.g. neuropsychology, neurovestibular or ophthalmology.

A patient with mTBI would need to be monitored for delayed post-traumatic pituitary dysfunction according to the guidance issued by the Society of British Neurological Surgeons.

In the medico-legal context, the diagnosis of mTBI is often unclear and speculative, as the radiological investigations are typically normal and symptoms are non-specific. Objective confirmation of mTBI may lead to an award for damages and care needs. An appropriate treatment for mTBI may include: removing the subject from activity; treatment in situ or in the community; further evaluating the subject in hospital without overnight admission (typically mTBI patients are discharged with promptly with head injury advice); or admission to hospital for a period of observation (typically 1-2 days). The subject may be further evaluated using tests (e.g. verbal, cognitive, motor and/or optical tests). CT scanning is generally only required if certain indications are present, including suspected skull fracture, post-traumatic seizure, focal neurological defect, repeated vomiting, a GCS score of less than 13 on initial assessment (less than 14 for children, or less than 15 for infants under 1 year), in accordance with NICE guidelines.

An appropriate treatment for m-sTBI may include: MRI or CT scanning (particularly within 1 hour of injury); admission to hospital (which may include admission to intensive care and/or transfer to a specialist clinic or major trauma centre with neurosurgical facilities); neuromonitoring; surgery; administering a therapy for alleviating TBI, such as administering neuroprotective drugs, e.g. drugs to treat cerebral swelling such as mannitol and hypertonic saline, and/or other neuroprotective measures, such as avoidance of hypertensive resuscitation and the use of sedation.

Thus, the present invention enables subjects with a TBI to be quickly stratified into mTBI or m-sTBI, so that they may receive the most appropriate treatment.

According to a further aspect of the invention, there is provided a detection system for diagnosing and/or monitoring TBI, the detection system comprising a sensor element comprising a substrate functionalized with a probe specific for a target miRNA The detection system can further comprise a detection device that is capable of detecting the binding of a target miRNA to the probe.

According to a yet further aspect of the invention, there is provided a sensor element for use in a detection system for diagnosing and/or monitoring TBI, the sensor element comprising a substrate functionalized with a probe specific for a target miRNA.

The sensor element may further comprise a sample addition zone for receiving a sample (e.g. a fluid sample) thereon.

The probe is capable of selectively binding the miRNA of interest. The substrate may be functionalized with a plurality of probes. The probes may all be the same, or two or more different probes may be provided. For example, in some embodiments, the substrate may be functionalized with a first probe specific for a first miRNA, and a second probe specific for a second miRNA. The first and second probes may be grouped together, for example on different portions of the sensor element.

In a further aspect of the invention, there is provided a composition for use in a method of diagnosing and/or monitoring traumatic brain injury (TBI) in a subject, the composition comprising a probe specific for a target miRNA. The composition may comprise any one of the listed miRNAs or with any plurality of the listed miRNAs (e.g., two, three, four, or more of the listed miRNAs).

In some embodiments, the target miRNA is selected from the group consisting of miR-505, miR-203, miR-654-3p, miR-655, miR-184, miR-301b, miR-425-5p, miR-502, miR-21, miR-let-7g, miR-335, miR-126*, miR-193a-5p, miR-144*, miR-190, miR-194, miR-365, miR-590-3p, miR-624, miR-625*, miR-671-3p, hsa-let-7c-5p, hsa-let-7i-5p, miR-142-3p, miR-148a-3p, miR-15b-5p, miR-16-5p, miR-181a-5p, miR-20a-5p, miR-20b-5p, miR-221-3p, miR-24-3p, miR-27b-3p, miR-29a-3p, miR-29c-3p, miR-30a-5p; miR-107; miR-135b-5p; miR-199b-5p; miR-324-5p; miR-652-3p, miR-424-5p, miR-10a, miR-132, miR-223, miR-143, miR-148b, miR-18a, miR-192, miR-429, miR-618, miR-95, miR-130a, miR-152, miR-27b, miR-301, miR-326, miR-345, miR-361, miR-422a, miR-579, miR-642, miR-99a, miR-520D-3p and miR-629.

In some embodiments, the target miRNA is selected from the group consisting of miR-505, miR-203, miR-654-3p, miR-655, miR-184, miR-301b, miR-425-5p, miR-502, miR-21, miR-let-7g, miR-335, hsa-miR-126*, miR-193a-5p, miR-144*, miR-190, miR-194, miR-365, miR-590-3p, miR-624, miR-625*, and miR-671-3p. These microRNAs have been found to be biomarkers expressed in all TBI patients (mild or severe).

In some embodiments, the target miRNA is selected from the group consisting of miR-505, miR-203, miR-654-3p, miR-655, miR-184, miR-301b, miR-425-5p, miR-502, miR-21, miR-let-7g and miR-335.

In some embodiments, the target miRNA is selected from the group consisting of let-7c-5p, let-7i-5p, miR-142-3p, miR-148a-3p, miR-15b-5p, miR-16-5p, miR-181a-5p, miR-20a-5p, miR-20b-5p, miR-221-3p, miR-24-3p, miR-27b-3p, miR-29a-3p, miR-29c-3p, and miR-424-5p; miR-30a-5p; miR-107; miR-135b-5p; miR-199b-5p; miR-324-5p; miR-652-3p.

In some embodiments the target miRNA is selected from the group consisting of miR-27b-3p, let-7i-5p, miR-142-3p, miR-107 and miR-135b-5p. In some embodiments at two target miRNAs are selected from the group consisting of miR-27b-3p, let-7i-5p, miR-142-3p, miR-107 and miR-135b-5p In some embodiments, the target miRNA is selected from the group consisting of miR-10a, miR-132, miR-223, miR-143, miR-148b, miR-18a, miR-192, miR-429, miR-618, miR-95, miR-130a, miR-152, miR-194, miR-27b, miR-301, miR-326, miR-345, miR-361, miR-422a, miR-579, miR-642, miR-99a, miR-520D-3p and miR-629.

In some embodiments, the target miRNA is selected from the group consisting of miR-425-5p, miR-502, miR-21 and miR-335.

The probe may comprise a biological molecule such as a protein (e.g. an antibody) or a nucleic acid. In some embodiments, the probe comprises a nucleic acid. The nucleic acid may comprise a sequence which is at least 70%, at least 75%, at least 80%, at least 85%, at least 90% or at least 95% identical to a sequence which is the complement of the full-length sequence of the target miRNA. In some embodiments, the nucleic acid comprises a sequence which is 100% identical to a sequence which is the complement of the sequence of the target miRNA (i.e. the receptor comprises a nucleic acid sequence which is the exact complement of the target miRNA sequence).

The probes may be attached to a surface of the substrate by any suitable means, such as by coupling chemistry known to those skilled in the art. In some embodiments, each probe is attached to a surface of the substrate via a linker. In some embodiments, the probe comprises a moiety for immobilizing the probe on the substrate, or for attaching the probe to a linker immobilized on the substrate.

Alternatively or in addition, the probe may comprise a detectable label. The detectable label may be, for example, radioactive, fluorescent, luminescent, or antibody-based (e.g., it may constitute a conventional tetrameric antibody or a detectable fragment thereof).

The substrate of the sensor element may be formed from any suitable material. In some embodiments, the substrate comprises or is formed from metal, plastic, glass, silica, silicon, graphite, graphene, or any combination thereof. In some embodiments, the substrate comprises multiple layers. For example, a substrate may be prepared by forming a surface or layer of graphene on a layer of silicon carbide or silica. The graphene surface may be chemically modified, for example to graphene-oxide (GO) or graphene-amine (GA). Methods for forming graphene layers, such as epitaxial growth and sublimation growth, will be known to those skilled in the art.

Conveniently, probes comprising or constituted by a nucleic acid can be attached to a GO surface via a linker, using an amide coupling reagent (e.g. (O-(7-azabenzotriazole-1-yl)-N,N,N',N'-tetramethyluronium hexafluorophosphate (HATU)). A sensor element comprising a surface functionalized with a nucleic acid probe can then be used to selectively detect its complementary miRNA.

Suitable linkers may comprise an aniline moiety (or a derivative thereof), a benzoic acid moiety (or a derivative thereof) or an ethendiamine moiety (or a derivative thereof). An aniline linker may be formed by attaching a nitrobenzene molecule (or derivative) to a graphene surface (e.g. using a diazonium salt), and reducing the nitrobenzene to aniline. The amine group of the aniline may then be used to attach to the probe. Similarly, a diazonium salt (e.g. 4-benzoic acid diazonium tetrafluoroborate) can be used to attach a benzoic acid or benzoic acid derivative to a graphene surface. An ethanediamine moiety may be attached to carboxylated graphene or graphene oxide.

The sensor element may be comprised within a test strip. The test strip may be disposable.

The detection device may be configured to detect the binding of a target miRNA to the receptor by any suitable means known to those skilled in the art, for example by detecting changes in electrical impedance, hydrogen ion concentration, or conformational changes resulting from hybridisation.

The detection device may further include a user interface to output data to a user.

In some embodiments, the detection device includes a database of treatment information. The device may be capable of identifying suitable treatment options from the database depending on the levels of the miRNA of interest. The treatment information may be provided to the user via the user interface.

Conveniently, the detection device may be portable, e.g. hand-held. The detection device may comprise a data storage unit for storing miRNA levels and other information relating to the subject. In some embodiments, the device comprises a data communication means for communicating data to other devices. For example, the device may communicate data wirelessly through WiFi, 3G, 4G, Bluetooth, or through a mobile app. This may conveniently enable the data to be easily accessed by medical professionals if necessary.

It is thus envisaged that the detection device of the invention provides an affordable, portable, point of care means for diagnosing and monitoring TBI non-invasively. The device may be used by ambulance crews, the military, schools, sports clubs and healthcare professionals, enabling the correct assessment and triage of patients suspected to have a TBI.

A further aspect of the present invention is a system for detecting and/or monitoring mTBI in a subject.

A type of detection system is based on complementarity between a target miRNA and a nucleic acid probe, generally an oligonucleotide probe. Therefore the present invention embraces a detection system for detecting and/or monitoring mTBI in a subject comprising a substrate functionalised with an oligonucleotide capable of binding to at least one of miR-27b-3p, let-7i-5p, miR-142-3p, miR-107 or miR-135b-5p. The oligonucleotide can have a sequence complementary to at least a portion of at least one of miR-27b-3p, let-7i-5p, miR-142-3p, miR-107 or miR-135b-5p, or the oligonucleotide can have a sequence complementary to at least a portion of SEQ ID NO: 25, 26, 35, 39 or 40. The complementary or base pairing region can be 7 or 8 or more nucleotides in length. In embodiments the complementary or base pairing region can be 9, 10, 12, 15 or more nucleotides in length or the complementary or base pairing region can be the full length of the miRNA. The substrate functionalised with an oligonucleotide can be a bead or a nanoparticle. The detection system can have further components capable of converting bound nucleic acid probe-miRNA into a detectable signal.

Another type of detection system is based on RT-PCT. Therefore the present invention embraces a detection system for detecting and/or monitoring mTBI in a subject comprising a primer pair designed for amplification of a cDNA complement of at least one miRNA selected from the group consisting of miR-27b-3p, let-7i-5p, miR-142-3p, miR-107 or miR-135b-5p.

In a further aspect there is provided a kit for use in the present methods. The kit may comprise at least probe (e.g. a protein, such as an antibody, or a nucleic acid) which is capable of selectively binding the miRNA of interest. In some embodiments, the kit comprises an array comprising a plurality of probes. In some embodiments, the at least one probe is a primer for carrying out PCR. The kit may further comprise instructions for use, for example instructions for use in the diagnosis and/or monitoring of TBI. The kit may further comprise suitable buffers and reagents, such as amplification primers and enzymes (e.g. DNA polymerase, reverse transcriptase for conversion of miRNA to cDNA).

It will be appreciated that statements made herein in relation to any aspect of the invention may equally apply to any other aspect of the invention, as appropriate.

DETAILED DESCRIPTION OF THE INVENTION

Embodiments of the invention will now be described by way of example and with reference to the accompanying Figures.

EXAMPLES

As miRNAs are emerging as promising biomarkers in a range of different pathologies, the present inventors sought to explore their role in TBI.

Example 1

Materials and Methods

Patients and Samples Collection

Study participants were recruited from the Surgical Reconstruction and Microbiology Research Centre (SRMRC) at Queen Elizabeth Hospital of Birmingham (UK) as part of Brain Biomarkers after Trauma (The Golden Hour Study) study (Ethics Ref. 13/WA/0399).

First, we performed screening of 754 miRNAs in 5 mTBI with extra-cranial injury (EC) patients, 5 sTBI+EC injury patients and healthy volunteers (HV) at 1 day and 15 days from injury with the aim to select specific candidate biomarkers able to discriminate mild from severe TBI and predict the recovery of mTBI after 15 days. Based on this information (Table 2), it was then possible to confirm the results study in an enlarged cohort of patients of 40 individuals grouped in 4 different categories: HV (n=10), EC (n=10), mTBI+EC (n=10), sTBI+EC (n=10). Healthy volunteers were consented and enrolled in the RECOS study. EC injury patients had radiographically-confirmed fractures, no head trauma, no infection, no history of neurological or psychiatric disorders and no alcohol or drug dependency. Mild TBI with EC included those with a non-penetrating head trauma and Glasgow Coma Scale (GCS) score >13. Severe TBI with EC included patients with GCS score of 8 or below. All patients were gender and age matched to HVs.

Sample Processing

Peripheral blood samples were taken at 1 day and 15 days from injury in each patient. The blood samples were processed for serum isolation within 2 h after withdrawal. Whole blood was left to stand for about 30' at room temperature before being centrifuged at 3000 rpm for 10' at 4° C. Serum was divided into aliquots and stored at −80° C. until analysis.

RNA Isolation, Reverse Transcription and miRNAs Profiling by TaqMan Low Density Array (TLDA)

Initial screening (discovery set) were performed on 5 mTBI+EC and 5 sTBI+EC patients, which were compared to HV at the two different time points (1 day and 15 days from the injury). The serum of these patients was used to profile the transcriptome of 754 miRNAs. Serum samples were centrifuged at 2000 rpm for 10' to pellet and remove any circulating cell or debris. MiRNAs were extracted from 400 µl of serum samples by using Qiagen miRNeasy mini kit (Qiagen, GmbH, Hilden, Germany), according to Qiagen supplementary protocol for purification of small RNAs from serum and plasma and finally eluted in 30 µl volume of RNase free water. The concentration and purity of the resulting RNA was determined with a ND-1000 UV-Vis Spectrophotometer (NanoDrop). 20 ng of serum RNAs was retrotranscribed and pre-amplified, according to the manufacturer's instructions. Pre-amplified products were loaded onto TLDAs, TaqMan Human MicroRNA Array v3.0 A and B (Applied Biosystems LifeTechnologies™). PCRs on TLDAs were performed on 7900HT Fast RealTime PCR System (Applied Biosystem, LifeTechnologies™).

Data Analysis

To obtain an accurate miRNA profiling, we used the global median normalization method. Similar to microarray analysis, Ct values from each sample were normalized to the median Ct of the array. Moreover, by computing the Pearson correlation among the Ct medians and means of each array and Ct of each miRNA, we identified two miRNAs that showed an expression profile close to the median and mean of TLDAs, i.e., miR-331 and miR-223*. These miRNAs were also confirmed to be among the most stable in TLDAs by applying two different methods [DataAssistv.3 software (AppliedBiosystem Life Technologies™)] and geNorm Algorithm. Accordingly, miR-331 and miR-223* were used as reference genes for validation by single TaqMan assays. Expression fold changes were calculated by the 2-ΔΔCT method. Differentially expressed miRNAs (DE miRNAs) were identified by Significance of Microarrays Analysis (SAM) computed by Multi experiment viewer v4.8.1, applying a two-class unpaired test among ΔCts and using a p-value based on 100 permutations; imputation engine: K-nearest neighbours (10 neighbours); false discovery rate<0.15 was used as correction for multiple comparisons. We accepted as reliable only DE miRNAs concordant by using all endogenous controls.

Single TaqMan Assays

Ten differentially expressed miRNAs were chosen from the arrays as potential candidate biomarkers with the aim to discriminate mild from severe TBI and to monitor the recovery of mild TBI. These candidates were used to validate the data in an enlarged cohort of 30 patients (validation set) grouped in 3 different categories (mTBI+EC, sTBI+EC and EC only) and 10 controls (HV) at two different time points (1 and 15 days from injury) by single TaqMan assays (AppliedBiosystems, Life Technologies™). Samples were extracted and retrotrascribed as described above and RT-qPCR analysis was performed in Bio-Rad iQ5 Real-time PCR Detection System (Bio-Rad, CA, USA). Expression fold changes were calculated by the 2-ΔΔCT method.

Statistical Analysis

The data were check for normal distribution and transformed to perform parametric tests. Comparisons across groups at each time and within groups over time were performed by the one-way analysis of variance and Tukey's post-hoc test on transformed data. A receiver operating characteristic analysis was utilised to calculate sensitivity and specificity of each biomarker in diagnosing either mTBI or sTBI expressed as area under the curve (AUC). All analyses were carried on SPSS v.20 (IBM). Differences were considered as statistically significant at p-value <0.05.

Results

Expression Profiles by TaqMan Low Density Arrays (TLDA)

From 754 screenable miRNAs of TLDA, we identified ten circulating miRNAs at 1 day and 13 at 15 days in mTBI+EC, 19 at 1 day and 22 at 15 days in sTBI+EC differentially expressed (Table 2). From this list, hsa-miR-126*, miR-193a-5p, miR-144*, miR-190, miR-194, miR-365, miR-590-3p, miR-624, miR-625* and miR-671-3p were excluded for further analysis because they were expressed in most of the patients, hence not suitable candidate biomarkers for mild or severe trauma only. However, the above microRNAs can identify TBI of any severity and are therefore useful TBI biomarkers. On the other hand, miR-184, miR-301b, miR-502 and miR-505 uniquely and differentially expressed in mTBI+EC at 1 day, were selected as early candidate biomarkers of mTBI. In addition, miR-203, miR-425-5p, miR-654-3p and miR-655 differentially expressed at 15 days post mTBI+EC were selected as candidate biomarkers able to track the recovery of mTBI.

Finally, two miRNAs, miR-21 and miR-335, constantly expressed at both time points in sTBI+EC, were selected for further studies.

TABLE 2

Fold change of microRNAs differentially expressed in 5 mTBI + EC (1 and 15 days) and 5 sTBI + EC (1 and 15 days) patients, compared to 5 HV and detected by TLDA.

| mTBI + EC 1 day VS HV | | mTBI + EC 15 days VS HV | | sTBI + EC 1 day VS HV | | sTBI + EC 15 days VS HV | |
|---|---|---|---|---|---|---|---|
| hsa-miR-184 | 0.1383 | hsa-miR-193a-5p | 24.901 | hsa-let-7g | 0.3250 | hsa-miR-130a | 14.979 |
| hsa-miR-190 | 0.1278 | hsa-miR-194 | 20.946 | hsa-miR-10a | 11.953 | hsa-miR-152 | 9.8921 |
| hsa-miR-425-5p | 0.0798 | hsa-miR-203 | 4.1763 | hsa-miR-132 | 8.1875 | hsa-miR-190 | 0.0277 |
| hsa-miR-502 | 0.0538 | hsa-miR-365 | 3.7087 | hsa-miR-143 | 26.193 | hsa-miR-193a-5p | 13.655 |
| hsa-miR-505 | 7.7696 | hsa-miR-425-5p | 3.0166 | hsa-miR-148b | 20.095 | hsa-miR-194 | 12.301 |
| hsa-miR-126* | 0.1570 | hsa-miR-654-3p | 0.0878 | hsa-miR-18a | 26.806 | hsa-miR-21 | 12.662 |
| hsa-miR-144* | 0.2758 | hsa-miR-655 | 0.0756 | hsa-miR-190 | 0.0634 | hsa-miR-27b | 18.977 |
| hsa-miR-590-3p | 0.3842 | hsa-miR-671-3p | 4.0584 | hsa-miR-192 | 0.2245 | hsa-miR-301 | 21.954 |
| hsa-miR-624 | 0.0836 | hsa-miR-126* | 0.2978 | hsa-miR-193a-5p | 29.785 | hsa-miR-326 | 93.099 |
| hsa-miR-301b | 0.0435 | hsa-miR-144* | 0.2645 | hsa-miR-21 | 7.1654 | hsa-miR-335 | 45.050 |
| | | hsa-miR-590-3p | 0.3035 | hsa-miR-223 | 4.6799 | hsa-miR-345 | 37.699 |
| | | hsa-miR-624 | 0.1643 | hsa-miR-335 | 37.192 | hsa-miR-361 | 37.295 |
| | | hsa-miR-625* | 0.1521 | hsa-miR-365 | 5.5771 | hsa-miR-422a | 77.373 |
| | | | | hsa-miR-429 | 0.1294 | hsa-miR-579 | 4.7203 |
| | | | | hsa-miR-618 | 29.527 | hsa-miR-642 | 41.515 |
| | | | | hsa-miR-95 | 20.788 | hsa-miR-671-3p | 8.4425 |
| | | | | hsa-miR-144* | 0.2759 | hsa-miR-99a | 12.218 |
| | | | | hsa-miR-624 | 0.0304 | hsa-miR-144* | 0.2905 |
| | | | | hsa-miR-625* | 0.0981 | hsa-miR-520D-3p | 0.2579 |
| | | | | | | hsa-miR-590-3p | 0.4188 |
| | | | | | | hsa-miR-625* | 0.1575 |
| | | | | | | hsa-miR-629 | 0.2793 |

Single TaqMan Assay for Candidate Biomarkers of mTBI

In order to validate these findings, we subsequently tested the expression of selected miRNAs in three separate and independent groups (10 mTBI+EC, 10 sTBI+EC, 10 EC) at the two chosen time points (1 and 15 days from injury) by using single TaqMan assays. The results were compared to 10 HV. The fold changes were calculated by the 2-$\Delta\Delta$CT method, using miR-331 and miR-223* as reference genes.

Figure 1A:
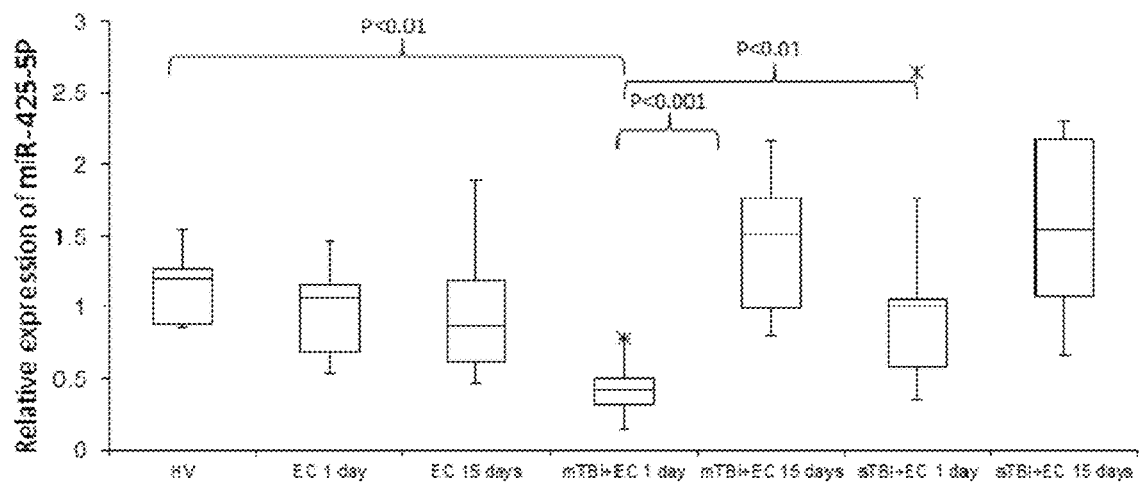
FIG. 1A-1B: miR-425-5p and miR-502 expression in 3 different categories of trauma and HV MiR-425-5p and miR-502 expression in 10 HV, 10 mTBI+EC (1 day), 10 mTBI+EC (15 days), 10 EC (1 day), 10 EC (15 days), 10 sTBI+EC (1 day) and 10 sTBI+EC (15 days) patients, detected by qRT-PCR analysis. MiR-425-5p expression was found to be remarkably decreased in mTBI+EC (1 day) compared to HV (p<0.01), mTBI+EC (15 dys) (p<0.001) and sTBI+EC (1 day) (p<0.01) (FIG. 1A). MiR-502 expression was found to be remarkably decreased in mTBI+EC (1 day) compared to HV (p<0.05), mTBI+EC (15 dys) (p<0.01) and sTBI+EC (1 day) (p<0.05) (FIG. 1B).
Figure 1B:
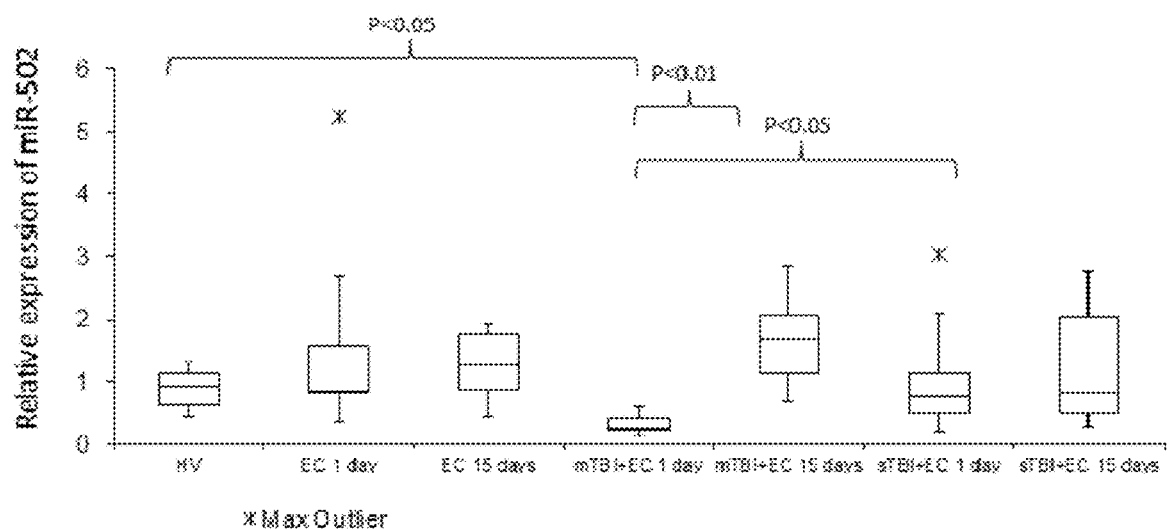

Among the candidate biomarkers of mTBI at both time points (miR-184, miR-301b, miR-502, miR-505, miR-203, miR-425-5p, miR-654-3p and miR-655), two showed interesting results and were significantly and differentially expressed in the three different categories compared to HV. In particular, miR-425-5p and miR-502 showed a similar trend (FIG. 1). They were both significantly downregulated in mTBI+EC (mean of 0.387±0.201 and 0.314±0.146) respectively at 1 day from injury compared to HV (p<0.001), EC (p<0.001) and sTBI+EC (p<0.001). At 15 days from mild injury, miR425-5p and miR-502 returned back to normal levels (0.886±0.310 and 1.157±0.258). The expression of miR-425-5p and miR-502 was also found similar to HV in EC samples at both 1 day and 15 days from injury, thus suggesting that these two biomarkers are differentially expressed in brain injury patients only. Moreover, neither of them showed any significant difference in sTBI+EC compared to HV at both time points. Therefore, miR-425-5p and miR-502 could be considered the most promising candidate biomarkers for the early diagnosis and monitoring of mTBI at 15 days after trauma. AUCs for these biomarkers are shown in Table 3.

Figure 2A:
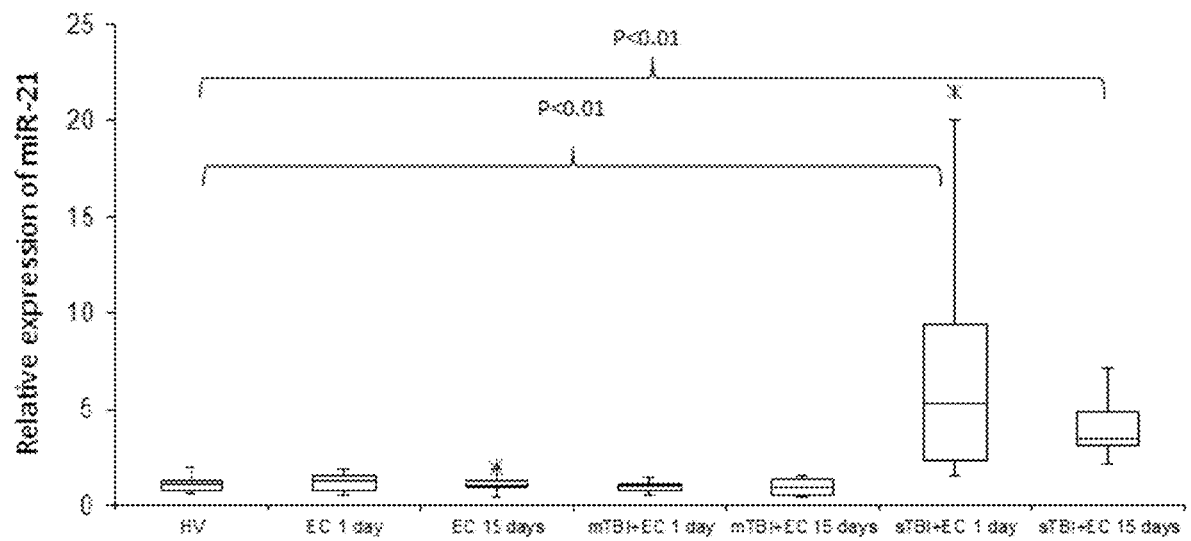
FIG. 2A-2B: miR-21 and miR-335 expression in 3 different categories of trauma and HV MiR-21 and miR-335 expression in 10 HV, 10 mTBI+EC (1 day), 10 mTBI+EC (15 days), 10 EC (1 day), 10 EC (15 days), 10 sTBI+EC (1 day) and 10 sTBI+EC (15 days) patients, detected by qRT-PCR analysis. MiR-21 expression was found to be significantly up-regulated in sTBI+EC (1 day and 15 days) compared to HV (p<0.01) (FIG. 2A). MiR-335 expression was found to be remarkably up-regulated in sTBI+EC (1 day) compared to HV (p<0.001), EC (15 days) (p<0.001) and mTBI+EC (1 day) (p<0.05) (FIG. 2B).
Figure 2B:
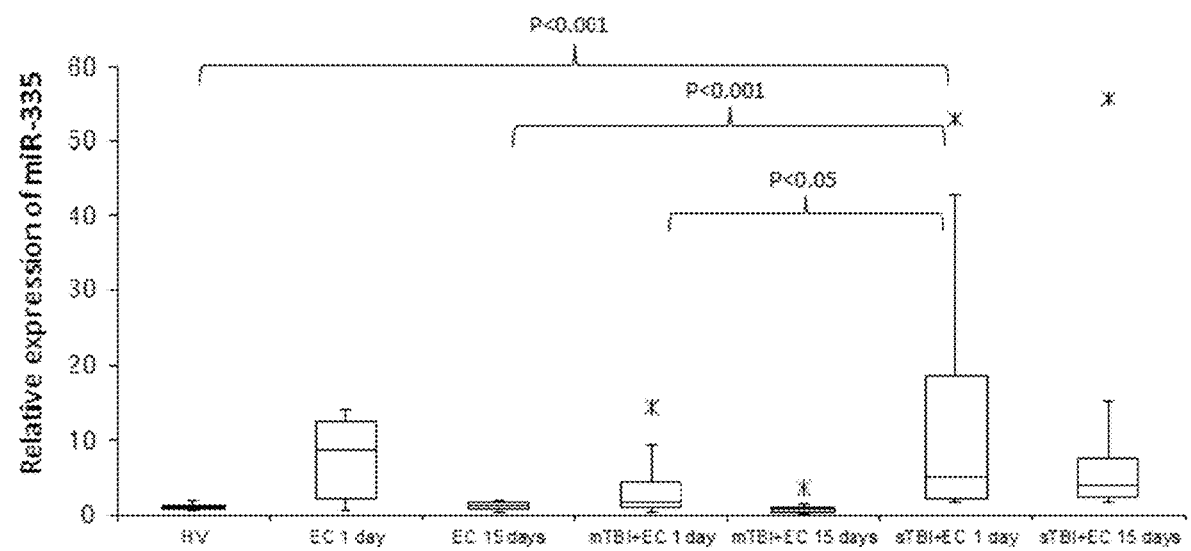

Single TaqMan Assay for Candidate Biomarkers of sTBI miR-21 and miR-335 were analysed as potential biomarkers of sTBI since they both appeared upregulated at both time points of sTBI+EC in the initial screening. They showed to be strong candidates in the second dataset of patients as well (FIG. 2). Mir-21 was significantly upregulated at both time points in sTBI with EC (7.106±4.192 and 4.012±1.577) with respect to HV (p, 0.001), EC (p<0.001) and mTBI (p<0.001). No significant differences were found in the remaining categories compared to HV. miR-335 showed upregulation in sTBI+EC and at both time points (16.824±14.195 and 12.324±8.931, respectively). On day 1, there this group were significantly different from controls (p=0.001) and mTBI+EC (p=0.031) but not EC. Interestingly, a significant upregulation in EC patients was found at 1 day (7.951±4.870), but not at 15 days from injury (1.260±0.531). For this reason, on day 15, miR335 was significantly higher in the sTBI+EC group with respect to HV (p=0.002), EC (p=0.007) and mTBI+EC (p=0.001). miR-335 did not show any significant difference in mTBI+EC at both time points compared to HV. AUCs for these biomarkers are also shown in Table 3.

TABLE 3

Area under the curve

| Variable(s) | Area | Asymptotic 95% Confidence Interval | |
|---|---|---|---|
| | | Lower Bound | Upper Bound |
| miR-502 1 day | .993 | .972 | 1.000 |
| miR-502 15 days | Not Significant | — | — |
| miR-425-5p 1 day | .994 | .977 | 1.000 |
| miR-425-5p 15 days | Not Significant | — | — |
| miR-21 1 day | .979 | .934 | 1.000 |
| miR-21 15 days | .975 | .929 | 1.000 |
| miR-335 1 day | .758 | .592 | .921 |
| miR-335 15 days | .957 | .884 | 1.000 |

Discussion

The present study investigated if changes in the levels of miRNAs can be applied to the diagnosis of TBI, and evaluating its severity. Four miRNAs were identified as being differentially expressed in TBI; miR-425-5p, miR 502, miR-21 and miR-335.

miR-425-5p showed significant results at day 1 in mTBI+EC compared to the HV and similar results were obtained in all other categories. Its downregulation within the first 24 h from the mild injury and the its return back to normal levels after 15 days, makes miR-425-5p a suitable candidate biomarker of mild trauma.

miR-502 was also found to be differentially expressed in mTBI+EC. The trend of this miRNA was very similar to miR-425-5p. It showed specificity for brain injured patients and could also be used to track recovery, since it returns back to normal value after 15 days form the mild injury.

Following sTBI, 2 miRNAs (miR-21, miR-335) were noted to be expressed at both 1 and 15 days and were thus selected as potential biomarkers for sTBI. miR-21 and miR-335 were significantly up-regulated at both time points when compared with controls in sTBI+EC. Therefore, the overexpression confirmed the results of the array and showed the potential of these molecules as biomarkers of sTBI.

The selected panel of miRNAs have the potential to diagnose TBI accurately and enable the stratification of patients according to severity which, in turn, allows the delivery of the most appropriate treatment.

Example 2

Patients and Sample Collection

Study participants were recruited from the Surgical Reconstruction and Microbiology Research Centre (SRMRC) at Queen Elizabeth Hospital of Birmingham (UK) as part of SIR (The Steroids and Immunity from injury through to Rehabilitation) study (Ethics Ref 11/SW/0177), ReCoS (The REpetitive COncussion in Sport) study (Ethics Ref. 11-0429AP28) and Golden Hour study (Ethics Ref. 13/WA/0399). Written informed consent was received from participants or valid proxy (family or a professional not directly involved in the study) prior to inclusion in the study.

The second dataset of samples used serum samples from a total of 120 individuals grouped in 4 different categories: HV (n=30), EC (n=30), mTBI+EC (n=30), sTBI+EC (n=30) and blood was taken at different time points (T0-1 h, T4-12 h, T48-72 h, 15 days) in each patient. Healthy volunteers were consented and enrolled in the ReCoS study. EC injury patients had radiographically-confirmed orthopaedic fractures, no head trauma, no infection, no history of neurological or psychiatric disorders and no alcohol or drug dependency. Mild TBI with EC included those with a non-penetrating head trauma and Glasgow Coma Scale (GCS) score ≥13. Severe TBI with EC included patients with GCS≤8.

Sample Processing

The blood samples were processed for serum isolation within 2 h after withdrawal. Whole blood was left to stand for about 30' at room temperature before being centrifuged at 3000 rpm for 10' at 4° C. Serum was divided into aliquots and stored at −80° C. until analysis.

RNA isolation, data analysis, assays and statistical analysis were carried out as described in Example 1.

Results

Single TaqMan Assay for Candidate Biomarkers of mTBI

In order to validate the findings of Example 1, the expression of selected miRNAs in 3 separate and independent groups (30 mTBI+EC, 30 sTBI+EC, 30 EC) was measured at different time points (T0, T4-12 h, T48-72 h and 15 days from the injury) by using single TaqMan assays. The results were compared to 10 HV. The fold changes were calculated by the $2\text{-}\Delta\Delta CT$ method, using miR-331 and miR-223* as reference.

Figure 3A:
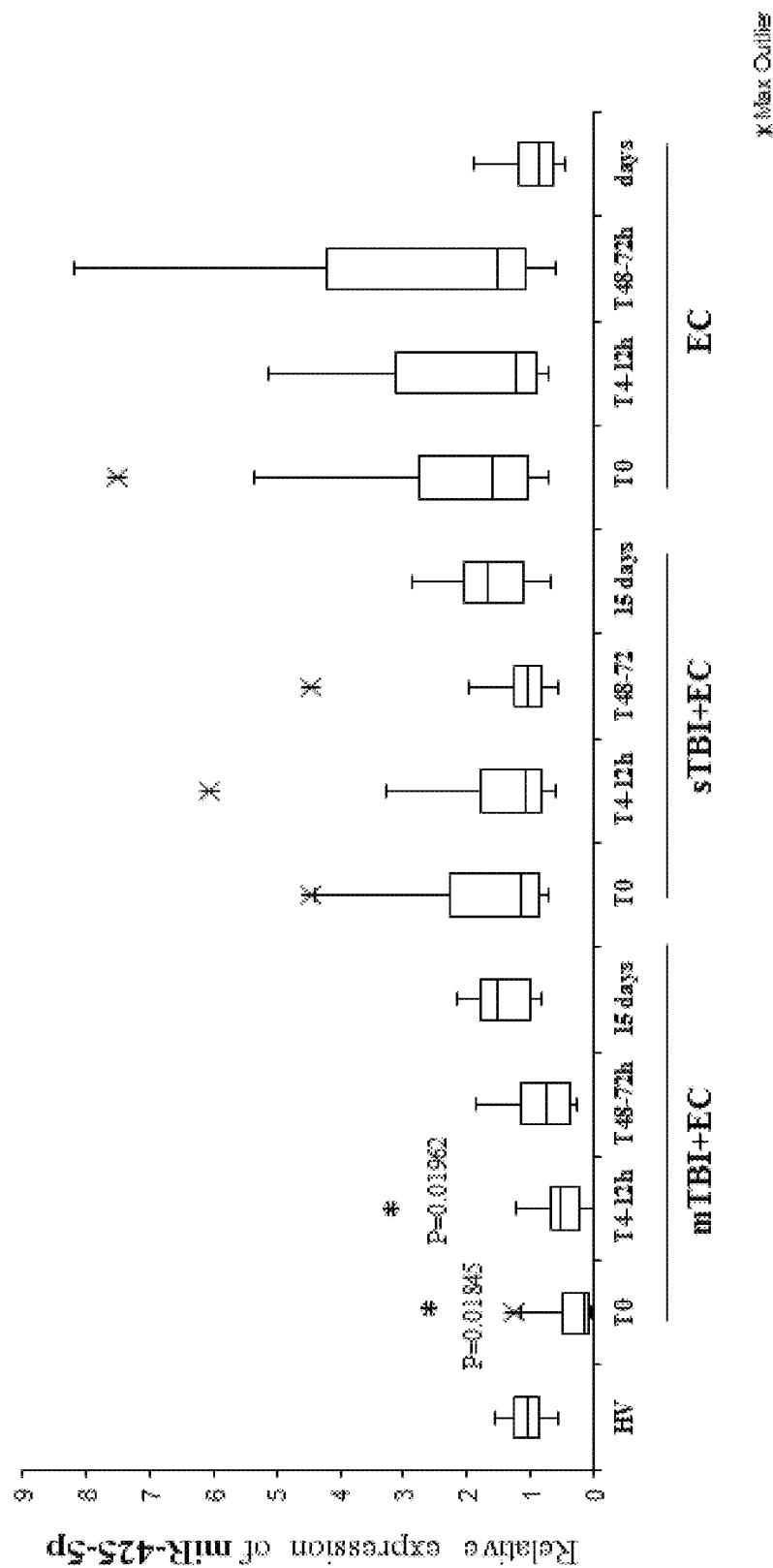
FIG. 3A-3B: Time course of miR-425-5p (FIG. 3A) and miR-502 (FIG. 3B) expression in 3 different categories of trauma and HV. MiR-425-5p and miR-502 expression in 30 HV, 30 mTBI+EC, 30 EC, 30 sTBI+EC patients at different time points from injury (T0, T4-12 h, T48-72 h, 15 days) detected by qRT-PCR analysis. MiR-425-5p expression was found to be remarkably decreased in mTBI+EC at T0 and T4-12 h compared to HV, sTBI+EC and EC (p<0.05). MiR-502 expression was found to be remarkably decreased in mTBI+EC at T0 and T4-12 h compared to HV, sTBI+EC and EC (p<0.05). P values were determined by Tukey's post-hoc test. * significantly different from HV
Figure 3B:
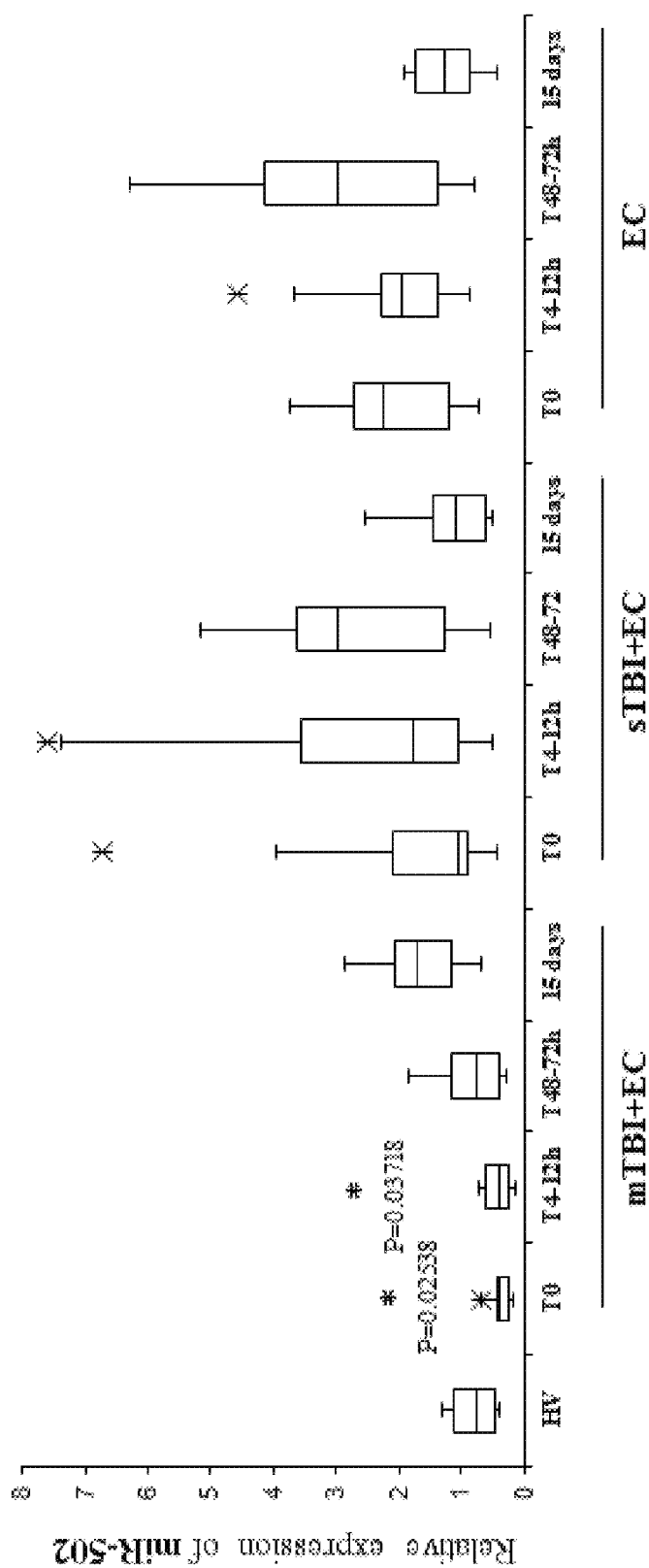

Among the candidate biomarkers of mTBI at both time points (miR-184, miR-502, miR-505, miR-301b, miR-203, miR-425-5p, miR-654-3p and miR-655), only two showed interesting results and were significantly and differentially expressed in the 3 different categories compared to HV. Specifically, miR-425-5p and miR-502 showed a similar trend (FIG. 3). They were both significantly downregulated in mTBI+EC, miR-425-5p at T0-1 h (p=0.01845), and at T4-12 h (p=0.01962) respectively compared to HV, or EC and sTBI+EC (p<0.05), and miR-502 at T0-1 h and at T4-12 h compared to HV (p=0.02538 and p=0.03718 respectively), or EC and sTBI+EC (p<0.01). After 48 h from mild injury, miR425-5p and miR-502 returned back to normal levels. The expression of miR-425-5p and miR-502 was also found in EC group at a comparable level to HV, thus suggesting that these two biomarkers are downregulated in brain injury patients only. Moreover, neither of them showed any significant downregulation in sTBI+EC compared to HV at all time points. Therefore, miR-425-5p and miR-502 could be considered the most promising candidate biomarkers for the early diagnosis and monitoring of mTBI. AUCs for these biomarkers at the most relevant time points, are shown in Table 4.

Single TaqMan Assay for Candidate Biomarkers of sTBI

Figure 4A:
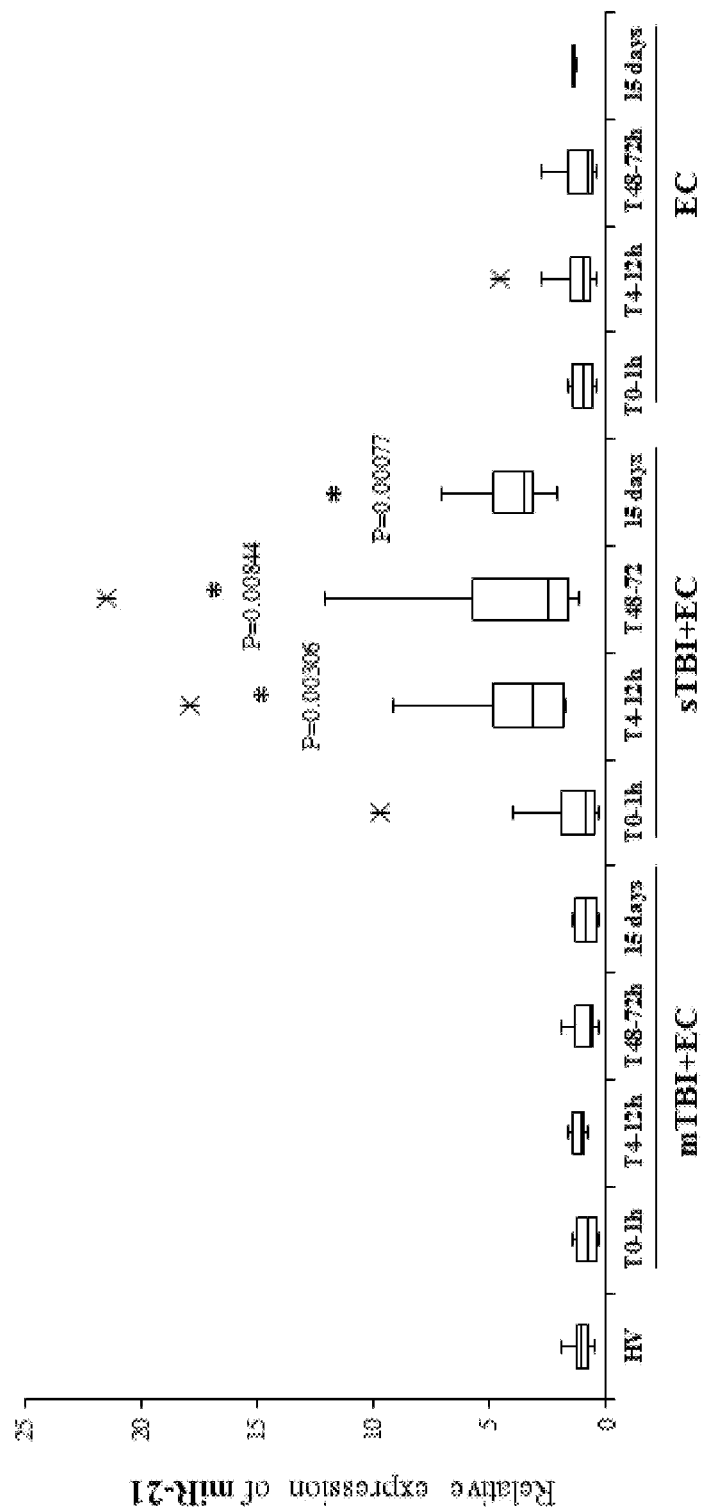
FIG. 4A-4B: Time course of miR-21 (FIG. 4A) and miR-335 (FIG. 4B) expression in 3 different categories of trauma and HV. MiR-21 and miR-335 expression in 30 HV, 30 mTBI+EC, 30 EC, and 30 sTBI+EC patients at different time points from injury (T0, T4-12 h, T48-72 h, 15 days) detected by qRT-PCR analysis. MiR-21 expression was found to be significantly up-regulated in sTBI+EC at T4-12 h, T48-72 h and 15 days compared to HV (p<0.01). MiR-335 expression was found to be remarkably up-regulated in sTBI+EC at T0, T4-12 h, T48-72 h and 15 days compared to HV and mTBI+EC (p<0.001) but not EC only. P values were determined by Tukey's post-hoc test.
Figure 4B:
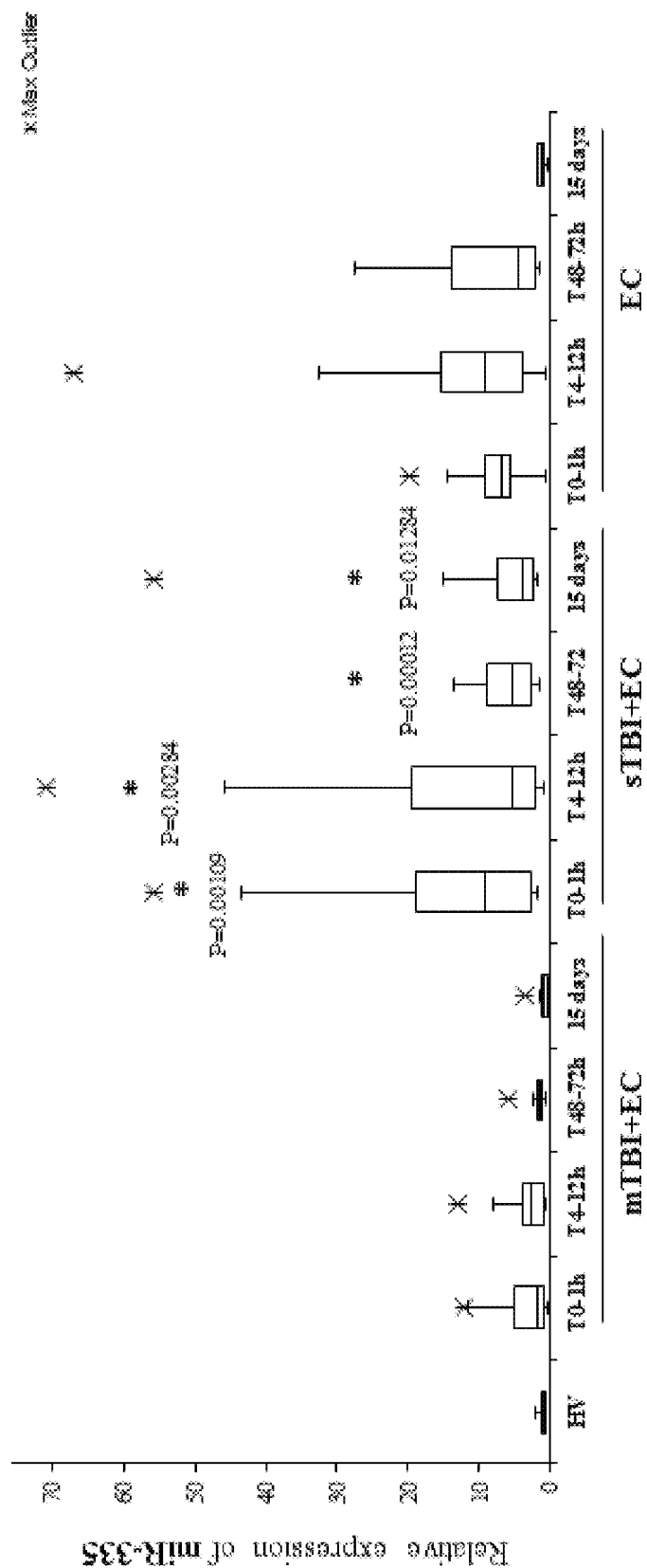

MiR-21 and miR-335 were analysed as potential biomarkers of sTBI since they both appeared upregulated at both time points of sTBI+EC in the initial screening. They showed to be strong candidates in the second dataset of patients also (FIG. 4). Mir-21 was significantly upregulated in sTBI with EC at all time points after 4 h from injury with respect to HV, EC and mTBI+EC (p=0.00306 at T4-12 h, p=0.00844 at T48-72 h and p=0.00077 at 15 days). No significant differences were found in the remaining categories compared to HV. MiR-335 showed upregulation in sTBI+EC and at all time points compared to HV (p=0.00109 at T0-1 h, p=0.00284 at T4-12 h, p=0.00012 T48-72 h and p=0.01284 at 15 days) and mTBI+EC but not significant upregulation was found compared to EC. AUCs for these biomarkers are also shown in Table 4.

TABLE 4

Area under the curve of the four candidate biomarkers of TBI at different time points. Only most relevant time points are shown.

| Variable(s) | Area | Sig | Asymptotic 95% Confidence Interval | |
|---|---|---|---|---|
| | | | Lower Bound | Upper Bound |
| miR-425-5p T0 | | | | |
| mTBI vs HV | 1 | .002 | 1 | 1 |
| mTBI vs sTBI | .911 | .020 | .778 | 1.000 |
| mTBI vs EC | .950 | .01 | .860 | 1.000 |
| miR-502 T0 | | | | |
| mTBI vs HV | 1 | .001 | 1.000 | 1.000 |
| mTBI vs sTBI | .990 | .001 | .960 | 1.000 |
| mTBI vs EC | .990 | .001 | .940 | 1.000 |
| miR-21 T4-12 h | | | | |
| sTBI vs HV | .961 | .003 | .880 | 1.000 |
| sTBI vs mTBI | .960 | .001 | .870 | 1.000 |
| sTBI vs EC | .900 | .004 | .740 | 1.000 |
| miR-335 T0 | | | | |
| sTBI vs HV | .990 | .000 | .960 | 1.000 |
| sTBI vs mTBI | .780 | .023 | .590 | .960 |
| sTBI vs EC | .500 | 1 | .240 | 0.780 |

Discussion

This study validated the previous finding that changes in the levels of miRNAs can be applied to the diagnosis of TBI, and evaluating its severity. The study confirmed that the following four miRNAs are differentially expressed in TBI; miR-425-5p, miR 502, miR-21 and miR-335.

miR-425-5p showed significant results at T0 and T4-12 h in mTBI+EC compared to the HV and similar results were obtained in all other categories. Its downregulation return back to normal levels after T48-72 h, confirms that miR-425-5p a suitable candidate biomarker of mild trauma.

miR-502 was also confirmed to be differentially expressed in mTBI+EC. The trend of this miRNA was very similar to miR-425-5p. It showed specificity for brain injured patients and could also be used to track recovery, since it returns back to normal value after T48-72 h form the mild injury.

Following sTBI, 2 miRNAs (miR-21, miR-335) were noted to be expressed at all time points analysed and were thus confirmed as potential biomarkers for sTBI. miR-21 and miR-335 were significantly up-regulated when compared with controls in sTBI+EC. Therefore, the overexpression confirmed the potential of these molecules as biomarkers of sTBI.

Example 3

Saliva samples were collected from concussed professional athletes after 2-3 days from injury and the microRNAs present in the saliva was analysed. The athletes were diagnosed clinically as having mTBI.

Materials and Methods

MicroRNAs were analysed using nCounter technology (nanoString Technologies®), which uses molecular "barcodes" and microscopic imaging to detect and count up to several hundred unique transcripts in one hybridization reaction. Each colour-coded barcode is attached to a single target-specific probe corresponding to a microRNAs of interest.

Analysis was carried out according to the manufacturer's protocol which includes the following steps:

Hybridization: The technology employs two ~20-base probes per microRNA that hybridize in solution. A reporter probe carries the signal, while a capture probe allows the complex to be immobilized for data collection.

Purification and Immobilization: After hybridization, the excess probes are removed and the probe/target complexes are aligned and immobilized in the nCounter Cartridge.

Data Collection: Sample cartridges are placed in a digital analyzer instrument for data collection. Colour codes on the surface of the cartridge are counted and tabulated for each target molecule.

Results

Table 5 below is a list of microRNAs which were found to be significantly and differentially expressed in concussed athletes compared to healthy volunteers. The table shows the fold change in expression of the microRNAs in the patients compared to the control group. The fold changes were calculated using miR-23a-3p and miR-148b-3p as reference genes. differentially expressed in concussed athletes compared to healthy volunteers. The table shows the fold change in expression of the microRNAs in the patients compared to the control group. The fold changes were calculated using miR-23a-3p and miR-148b-3p as reference genes.

TABLE 5 microRNAs significantly and differentially expressed in concussed athletes compared to healthy volunteers

| microRNA | Fold change |
|---|---|
| hsa-let-7c-5p | 2.80 |
| hsa-let-7i-5p | 1.82 |
| hsa-miR-142-3p | 1.41 |
| hsa-miR-148a-3p | 1.72 |
| hsa-miR-15b-5p | 2.30 |
| hsa-miR-16-5p | 2.32 |
| hsa-miR-181a-5p | 1.54 |
| hsa-miR-20a-5p + hsa-miR-20b-5p§ | 2.16 |
| hsa-miR-221-3p | 2.90 |
| hsa-miR-24-3p | 1.94 |
| hsa-miR-27b-3p | 3.45 |
| hsa-miR-29a-3p | 4.03 |
| hsa-miR-29c-3p | 1.44 |
| hsa-miR-424-5p | 2.88 |
| hsa-miR-30a-5p | 2.16 |
| hsa-miR-107 | 1.72 |
| hsa-miR-135b-5p | 1.97 |
| hsa-miR-199b-5p | 1.88 |
| hsa-miR-324-5p | 5.61 |
| hsa-miR-652-3p | 3.43 |

§the values for miR-20a-5p and miR-20b-5p were combined due to the nCounter technology not being able to distinguish between them.

Discussion

This study shows that microRNAs present in saliva are an indicator of concussion/mTBI. This is significant because saliva is more easily obtained than blood, and thus detection of salivary microRNAs offers a rapid and convenient means for diagnosing TBI, particularly pitch-side.

Example 4

Materials and Methods

Study Approval

Study participants were recruited through the Surgical Reconstruction and Microbiology Research Centre (SRMRC), based at Queen Elizabeth Hospital of Birmingham (UK), as part of the ReCoS (The REpetitive COncussion in Sport) study (Ethics Ref. 11-0429AP28). Written informed consent was received from participants prior to inclusion in the study.

Saliva samples from a total of 20 subjects (discovery group) were analysed. In particular, saliva samples of 10 concussed and 10 non-concussed athletes were used to screen proteins and 6 concussed and 6 non-concussed athletes for microRNA analysis. Saliva of concussed players was collected 48-72 hours after concussion certified by the attending enhanced care team in accordance with the current protocol for the relevant sport. From these data, we calculated the sample size needed for validation in a larger cohort of patients with alpha=0.05 and power=0.9. The sample size required was 29 subjects based on the most variant miRNA identified in the discovery group.

A second set of samples (validation group) was obtained from a total of 22 concussed and 10 non concussed players. Samples were collected between 2 and 5 days after concussion.

Sample Processing

Five ml of saliva were collected in a 50 ml sterile plastic universal container tube kept on ice for no more than 30'. Samples were then centrifuged at 2600×g for 15' at 4° C. Saliva was then divided into aliquots and to each ml of saliva, RNase inhibitor (500 units/mL) was added for the analysis of miRNAs.

Samples were stored at −80.0 until analysis.

RNA Isolation

Total RNA was isolated from 400 μl of saliva by using Qiagen miRNeasy Mini Kit (Qiagen, GmbH, Hilden, Germany), according to Qiagen Supplementary Protocol for purification of RNA (including small RNAs) from serum or plasma. Finally, RNA was eluted in 200 μl RNAse-free water and subsequently precipitated by adding 20 μg glycogen, 0.1 volumes 3 M sodium acetate and 2.5 volumes ice cold 100% ethanol. After incubation at −80° C. overnight, RNA was centrifuged and washed twice in ice cold 75% ethanol and resuspended in 7 μl RNAse-free water. RNA was quantified by Nanodrop.

Circulating miRNA Profiling Through NanoString Technology

Expression profile of miRNAs from saliva was performed through NanoString technology by using nCounter Human v3 miRNA Expression Assay Kits (NanoString Technologies) in an nCounter FLEX (Prep Station and Digital Analyzer) (NanoString Technologies), according to manufacturer instructions. Profiling was performed on 6 concussed and 6 non concussed athletes. Three μl (approximately 150 ng) of total RNA were used for sample preparation. Data analysis was performed through nSolver 2.6 software; miRNAs used as endogenous controls were selected through global median normalization (GMN) method: we computed Pearson correlation between the count means for each lane and the counts of each miRNA, identifying those miRNAs whose expression was closer to the count mean of the cartridge (miR-23a-3p, miR-29b-3p, miR-148b-3p). Statistical analysis was performed through Significance of Microarrays Analysis (SAM) (http://www.tm4.org), using a p-value based on 100 permutations; imputation engine: K-nearest neighbours (10 neighbours); false discovery rate (FDR)<0.05.

Single TaqMan Assays

Twenty-one differentially expressed miRNAs were chosen from the arrays as potential candidate biomarkers of concussion. These candidates were used to validate the data in an enlarged cohort of 22 concussed athletes and 10 non concussed athletes (validation group). Saliva was collected after 2-5 days from injury and analysed by single TaqMan assays (AppliedBiosystems, Life Technologies™). Samples were extracted as described above, retrotranscribed (AppliedBiosystems, Life Technologies™) and RT-qPCR analysis was performed in a Bio-Rad iQ5 Real-time PCR Detection System (Bio-Rad, CA, USA). Expression fold changes were calculated by the 2-ΔΔCT method by using miR-23a-3p and miR-148b-3p as reference genes.

Statistical Analysis

A non parametric test (Mann-Whitney U test) was used to compare the level of miRNAs in the two independent groups. A p value <0.05 was accepted as significant. In addition, a Receiver Operating Characteristic (ROC) analysis was utilised to calculate sensitivity and specificity of each biomarker in diagnosing concussion, expressed as Area Under the Curve (AUC). All analyses were carried on SPSS v.22 (IBM).

Results

Nanostring Profiling

Among the 800 microRNAs analysed by nCounter NanoString in saliva of concussed and non-concussed athletes, 21 miRNAs were selected as differentially expressed across the two populations: hsa-let-7c-5p, hsa-let-7i-5p, hsa-miR-15b-5p, hsa-miR-16-5p, hsa-miR-20a-5p+hsa-miR-20b-5p, hsa-miR-24-3p, hsa-miR-27b-3p, hsa-miR-29a-3p, hsa-miR-29c-3p, hsa-miR-30a-5p, hsa-miR-107, hsa-miR-135b-5p, hsa-miR-142-3p, hsa-miR-148a-3p, hsa-miR-181a-5p, hsa-miR-199b-5p, hsa-miR-221-3p, hsa-miR-324-5p, hsa-miR-424-5p, hsa-miR-652-3p. Results showed a significant upregulation for all the miRNAs mentioned above.

Single TaqMan Assay

In order to validate these findings, we subsequently tested the expression of the 21 selected miRNAs in a separate and independent group, composed of 22 concussed athletes and 10 non concussed athletes. Saliva was collected after 2-5 days from injury, by using single TaqMan assays. Fold changes were calculated by the 2-ΔΔCT method, using miR-23a-3p and miR-148b-3p as reference markers.

Among these candidate biomarkers for concussion 5 were significantly upregulated in the validation group. Specifically, miR-27b-3p (p=0.02), let-7i-5p (p=0.001), miR-142-3p (p=0.008), miR-107 (p=0.03), miR-135b-5p (p=0.02) confirmed the results obtained by Nanostring analysis (FIG. 5). These results are also shown in Table 6 which shows that the control group have a fold change of between 0.6 and 1.4. A fold change above this is considered indicative of concussion. The median fold change seen for the concussed athletes is a fold change of approximately 2.5 for each of the identified 5 miRNAs. A fold change value calculated by the 2-ΔΔCT method of 2.0 or greater for any of these identified 5 biomarkers would give a diagnosis of concussion.

TABLE 6

Expression of the 5 miRNAs that were significantly upregulated in the validation group.

|  | miR 27b-3p | let 7i-5p | miR 142-3p | miR 107 | miR 135b-5p |
|---|---|---|---|---|---|
| control | 0.6-1.4 | 0.6-1.4 | 0.6-1.4 | 0.6-1.4 | 0.6-1.4 |
| concussed average | 4.494754264 | 4.691358 | 5.35579639 | 3.33647 | 6.022724008 |
| concussed median | 2.462406429 | 3.266526 | 2.98367692 | 2.387747 | 2.539442 |

Boxplot of relative expression and AUCs for these biomarkers (0.755, 0.845, 0.791, 0.732 and 0.755 respectively) are shown in FIG. 6 and in Table 7.

TABLE 7

Area Under the Curve (AUC) of miRNAs selected as biomarkers of concussion

| Variables | AUC |
|---|---|
| miR-27b-3p | 0.755 |
| let-7i-5p | 0.845 |
| miR-142-3p | 0.791 |
| miR-107 | 0.732 |
| miR-135b-5p | 0.755 |

Discussion

In this study, we examined saliva, a potentially novel fluid for the examination of biomarkers in the context of head injury and concussion (mTBI).

Five miRNAs were found significantly upregulated in the saliva of the concussed population only. Each of miRNA-27b-3p, let-7i-5p, miR-142-3p, miR-107 and miR-135b-5p were significantly upregulated in concussed athletes. Each of these five biomarkers have the ability to distinguish concussed athletes from non-concussed athletes especially after 2-5 days from injury.

What is claimed is:

1. A method of diagnosing and treating mild traumatic brain injury (mTBI) in a subject in need thereof, the method comprising:
- (a) obtaining a saliva sample from the subject;
- (b) contacting the saliva sample with a probe comprising a nucleic acid able to bind to at least one miRNA selected from the group consisting of miR-27b-3p, let-7i-5p, miR-142-3p, miR-107 and miR-135b-5p;
- (c) determining an amount of the at least one target miRNA in the saliva sample, wherein the at least one target miRNA comprises:
  - (i) miR-142-3p;
  - (ii) miR-107;
  - (iii) miR-135b-5p; or
  - (iv) miR-27b-3p, let-7i-5p, miR-142-3p, miR-107, and miR-135b-5p collectively;
- (d) identifying the subject as having mTBI where the amount of the at least one target miRNA is increased relative to a predetermined threshold value or relative to the amount of the at least one target miRNA in a control sample; and
- (e) treating the subject identified as having mTBI:
  - by administering to the subject one or more neuroprotective therapies selected from the group consisting of an effective amount of a neuroprotective drug, mannitol, hypertonic saline, avoidance of hypertensive resuscitation, and sedation.

2. The method of claim 1 wherein the at least one target miRNA is miR-142-3p.

3. The method of claim 1 wherein the at least one target miRNA is miR-107.

4. The method of claim 1 wherein the at least one target miRNA is miR-135b-5p.

5. The method of claim 1, wherein the saliva sample is obtained during a period of time after the injury selected from 24 hours to 15 days, 24 hours to 7 days, and 2 to 5 days.

6. The method of claim 1, further comprising obtaining one or more additional saliva samples from the subject at one or more additional times after the injury and repeating the contacting, determining, identifying, and treating steps for each additional sample.

7. The method of claim 6, wherein the one or more additional saliva samples is obtained at day 2, 3, 5, 7, 10, 14, or 15 after the injury.

8. The method of claim 1, wherein the detecting an amount of the at least one miRNA is performed using a PCR-based assay.

9. The method of claim 8, wherein the predetermined threshold is equivalent to a fold change of 1.5 or more using the 2-delta delta CT (2-ΔΔCT) method.

10. The method of claim 8, wherein the predetermined threshold is equivalent to a fold change of 2 or more using the 2-delta delta CT (2-ΔΔCT) method.

11. The method of claim 1, wherein the method comprises determining a level of at least two of the target miRNAs in the saliva sample.

12. The method of claim 11, wherein the at least two target miRNAs are selected from miR-27b-3p, let-7i-5p, miR-142-3p, miR-107 or miR-135b-5p.

13. The method of claim 1, wherein the the at least one target miRNA comprises miR-27b-3p, let-7i-5p, miR-142-3p, miR-107 and miR-135b-5p collectively.

14. The method of claim 1, wherein the method further comprises determining the amount of one or more additional miRNAs selected from let-7c-5p, let-7i-5p, miR-142-3p, miR-148a-3p, miR-15b-5p, miR-16-5p, miR-181a-5p, miR-20a-5p, miR-20b-5p, miR-221-3p, miR-24-3p, miR-27b-3p, miR-29a-3p, miR-29c-3p, miR-424-5p, miR-30a-5p, miR-107, miR-135b-5p, miR-199b-5p, miR-324-5p, and miR-652-3p.

* * * * *

SEQUENCE LISTING

```
<160> NUMBER OF SEQ ID NOS: 69

<210> SEQ ID NO 1
<211> LENGTH: 22
<212> TYPE: RNA
<213> ORGANISM: Homo sapiens

<400> SEQUENCE: 1
uagcuuauca gacugauguu ga                                           22

<210> SEQ ID NO 2
<211> LENGTH: 23
<212> TYPE: RNA
<213> ORGANISM: Homo sapiens

<400> SEQUENCE: 2
aaugacacga ucacucccgu uga                                          23

<210> SEQ ID NO 3
<211> LENGTH: 21
<212> TYPE: RNA
<213> ORGANISM: Homo sapiens

<400> SEQUENCE: 3
auccuugcua ucugggugcu a                                            21

<210> SEQ ID NO 4
<211> LENGTH: 23
<212> TYPE: RNA
<213> ORGANISM: Homo sapiens

<400> SEQUENCE: 4
ucaagagcaa uaacgaaaaa ugu                                          23

<210> SEQ ID NO 5
```

-continued

```
<211> LENGTH: 23
<212> TYPE: RNA
<213> ORGANISM: Homo sapiens

<400> SEQUENCE: 5
cagugcaaug auauugucaa agc                                              23

<210> SEQ ID NO 6
<211> LENGTH: 22
<212> TYPE: RNA
<213> ORGANISM: Homo sapiens

<400> SEQUENCE: 6
uggacggaga acugauaagg gu                                               22

<210> SEQ ID NO 7
<211> LENGTH: 22
<212> TYPE: RNA
<213> ORGANISM: Homo sapiens

<400> SEQUENCE: 7
cgucaacacu ugcugguuuc cu                                               22

<210> SEQ ID NO 8
<211> LENGTH: 22
<212> TYPE: RNA
<213> ORGANISM: Homo sapiens

<400> SEQUENCE: 8
gugaaauguu uaggaccacu ag                                               22

<210> SEQ ID NO 9
<211> LENGTH: 22
<212> TYPE: RNA
<213> ORGANISM: Homo sapiens

<400> SEQUENCE: 9
uaugucugcu gaccaucacc uu                                               22

<210> SEQ ID NO 10
<211> LENGTH: 22
<212> TYPE: RNA
<213> ORGANISM: Homo sapiens

<400> SEQUENCE: 10
auaauacaug guuaaccucu uu                                               22

<210> SEQ ID NO 11
<211> LENGTH: 21
<212> TYPE: RNA
<213> ORGANISM: Homo sapiens

<400> SEQUENCE: 11
gccccugggc cuauccuaga a                                                21

<210> SEQ ID NO 12
<211> LENGTH: 22
<212> TYPE: RNA
<213> ORGANISM: Homo sapiens

<400> SEQUENCE: 12
cguguauuug acaagcugag uu                                               22
```

-continued

```
<210> SEQ ID NO 13
<211> LENGTH: 22
<212> TYPE: RNA
<213> ORGANISM: Homo sapiens

<400> SEQUENCE: 13
ugagguagua guuguacag uu                                              22

<210> SEQ ID NO 14
<211> LENGTH: 21
<212> TYPE: RNA
<213> ORGANISM: Homo sapiens

<400> SEQUENCE: 14
cauuauuacu uuugguacgc g                                              21

<210> SEQ ID NO 15
<211> LENGTH: 22
<212> TYPE: RNA
<213> ORGANISM: Homo sapiens

<400> SEQUENCE: 15
ugggucuuug cgggcgagau ga                                             22

<210> SEQ ID NO 16
<211> LENGTH: 22
<212> TYPE: RNA
<213> ORGANISM: Homo sapiens

<400> SEQUENCE: 16
ggauaucauc auauacugua ag                                             22

<210> SEQ ID NO 17
<211> LENGTH: 21
<212> TYPE: RNA
<213> ORGANISM: Homo sapiens

<400> SEQUENCE: 17
cuauauauca aacauauucc u                                              21

<210> SEQ ID NO 18
<211> LENGTH: 22
<212> TYPE: RNA
<213> ORGANISM: Homo sapiens

<400> SEQUENCE: 18
uguaacagca acuccaugug ga                                             22

<210> SEQ ID NO 19
<211> LENGTH: 22
<212> TYPE: RNA
<213> ORGANISM: Homo sapiens

<400> SEQUENCE: 19 uaaugcccu aaaaauccuu au                                              22

<210> SEQ ID NO 20
<211> LENGTH: 21
<212> TYPE: RNA
<213> ORGANISM: Homo sapiens

<400> SEQUENCE: 20
uaauuuuaug uauaagcuag u                                              21
```

```
<210> SEQ ID NO 21
<211> LENGTH: 22
<212> TYPE: RNA
<213> ORGANISM: Homo sapiens

<400> SEQUENCE: 21
uaguaccagu accuuguguu ca                                              22

<210> SEQ ID NO 22
<211> LENGTH: 22
<212> TYPE: RNA
<213> ORGANISM: Homo sapiens

<400> SEQUENCE: 22
gacuauagaa cuuucccccu ca                                              22

<210> SEQ ID NO 23
<211> LENGTH: 21
<212> TYPE: RNA
<213> ORGANISM: Homo sapiens

<400> SEQUENCE: 23
uccgguucuc agggcuccac c                                               21

<210> SEQ ID NO 24
<211> LENGTH: 22
<212> TYPE: RNA
<213> ORGANISM: Homo sapiens

<400> SEQUENCE: 24
ugagguagua gguuguaugg uu                                              22

<210> SEQ ID NO 25
<211> LENGTH: 22
<212> TYPE: RNA
<213> ORGANISM: Homo sapiens

<400> SEQUENCE: 25
ugagguagua guuugugcug uu                                              22

<210> SEQ ID NO 26
<211> LENGTH: 23
<212> TYPE: RNA
<213> ORGANISM: Homo sapiens

<400> SEQUENCE: 26
uguaguguuu ccuacuuuau gga                                             23

<210> SEQ ID NO 27
<211> LENGTH: 22
<212> TYPE: RNA
<213> ORGANISM: Homo sapiens

<400> SEQUENCE: 27
ucagugcacu acagaacuuu gu                                              22

<210> SEQ ID NO 28
<211> LENGTH: 22
<212> TYPE: RNA
<213> ORGANISM: Homo sapiens

<400> SEQUENCE: 28
uagcagcaca ucaugguuua ca                                              22
```

<210> SEQ ID NO 29
<211> LENGTH: 22
<212> TYPE: RNA
<213> ORGANISM: Homo sapiens

<400> SEQUENCE: 29
uagcagcacg uaaauauugg cg                                    22

<210> SEQ ID NO 30
<211> LENGTH: 23
<212> TYPE: RNA
<213> ORGANISM: Homo sapiens

<400> SEQUENCE: 30
aacauucaac gcugucggug agu                                   23

<210> SEQ ID NO 31
<211> LENGTH: 23
<212> TYPE: RNA
<213> ORGANISM: Homo sapiens

<400> SEQUENCE: 31
uaaagugcuu auagugcagg uag                                   23

<210> SEQ ID NO 32
<211> LENGTH: 23
<212> TYPE: RNA
<213> ORGANISM: Homo sapiens

<400> SEQUENCE: 32
caaagugcuc auagugcagg uag                                   23

<210> SEQ ID NO 33
<211> LENGTH: 23
<212> TYPE: RNA
<213> ORGANISM: Homo sapiens

<400> SEQUENCE: 33
agcuacauug ucugcugggu uuc                                   23

<210> SEQ ID NO 34
<211> LENGTH: 22
<212> TYPE: RNA
<213> ORGANISM: Homo sapiens

<400> SEQUENCE: 34
uggcucaguu cagcaggaac ag                                    22

<210> SEQ ID NO 35
<211> LENGTH: 21
<212> TYPE: RNA
<213> ORGANISM: Homo sapiens

<400> SEQUENCE: 35
uucacagugg cuaaguucug c                                     21

<210> SEQ ID NO 36
<211> LENGTH: 22
<212> TYPE: RNA
<213> ORGANISM: Homo sapiens

<400> SEQUENCE: 36

```
uagcaccauc ugaaaucggu ua                                        22

<210> SEQ ID NO 37
<211> LENGTH: 22
<212> TYPE: RNA
<213> ORGANISM: Homo sapiens

<400> SEQUENCE: 37
uagcaccauu ugaaaucggu ua                                        22

<210> SEQ ID NO 38
<211> LENGTH: 22
<212> TYPE: RNA
<213> ORGANISM: Homo sapiens

<400> SEQUENCE: 38
uguaaacauc cucgacugga ag                                        22

<210> SEQ ID NO 39
<211> LENGTH: 23
<212> TYPE: RNA
<213> ORGANISM: Homo sapiens

<400> SEQUENCE: 39
agcagcauug uacagggcua uca                                       23

<210> SEQ ID NO 40
<211> LENGTH: 23
<212> TYPE: RNA
<213> ORGANISM: Homo sapiens

<400> SEQUENCE: 40
uauggcuuuu cauuccuaug uga                                       23

<210> SEQ ID NO 41
<211> LENGTH: 23
<212> TYPE: RNA
<213> ORGANISM: Homo sapiens

<400> SEQUENCE: 41
cccaguguuu agacuaucug uuc                                       23

<210> SEQ ID NO 42
<211> LENGTH: 23
<212> TYPE: RNA
<213> ORGANISM: Homo sapiens

<400> SEQUENCE: 42 cgcaucoccu agggcauugg ugu                                       23

<210> SEQ ID NO 43
<211> LENGTH: 21
<212> TYPE: RNA
<213> ORGANISM: Homo sapiens

<400> SEQUENCE: 43
aauggcgcca cuagguugu g                                          21

<210> SEQ ID NO 44
<211> LENGTH: 22
<212> TYPE: RNA
<213> ORGANISM: Homo sapiens

<400> SEQUENCE: 44
```

```
cagcagcaau ucauguuuug aa                                          22

<210> SEQ ID NO 45
<211> LENGTH: 23
<212> TYPE: RNA
<213> ORGANISM: Homo sapiens

<400> SEQUENCE: 45
uacccuguag auccgaauuu gug                                         23

<210> SEQ ID NO 46
<211> LENGTH: 22
<212> TYPE: RNA
<213> ORGANISM: Homo sapiens

<400> SEQUENCE: 46
uaacagucua cagccauggu cg                                          22

<210> SEQ ID NO 47
<211> LENGTH: 22
<212> TYPE: RNA
<213> ORGANISM: Homo sapiens

<400> SEQUENCE: 47
ugucaguuug ucaauaccc ca                                           22

<210> SEQ ID NO 48
<211> LENGTH: 21
<212> TYPE: RNA
<213> ORGANISM: Homo sapiens

<400> SEQUENCE: 48
ugagaugaag cacuguagcu c                                           21

<210> SEQ ID NO 49
<211> LENGTH: 22
<212> TYPE: RNA
<213> ORGANISM: Homo sapiens

<400> SEQUENCE: 49
ucagugcauc acagaacuuu gu                                          22

<210> SEQ ID NO 50
<211> LENGTH: 23
<212> TYPE: RNA
<213> ORGANISM: Homo sapiens

<400> SEQUENCE: 50
uaaggugcau cuagugcaga uag                                         23

<210> SEQ ID NO 51
<211> LENGTH: 21
<212> TYPE: RNA
<213> ORGANISM: Homo sapiens

<400> SEQUENCE: 51
cugaccuaug aauugacagc c                                           21

<210> SEQ ID NO 52
<211> LENGTH: 22
<212> TYPE: RNA
<213> ORGANISM: Homo sapiens
```

```
<400> SEQUENCE: 52
uaauacuguc ugguaaaacc gu                                          22

<210> SEQ ID NO 53
<211> LENGTH: 23
<212> TYPE: RNA
<213> ORGANISM: Homo sapiens

<400> SEQUENCE: 53
aaacucuacu uguccuucug agu                                         23

<210> SEQ ID NO 54
<211> LENGTH: 21
<212> TYPE: RNA
<213> ORGANISM: Homo sapiens

<400> SEQUENCE: 54
ucaauaaaug ucuguugaau u                                           21

<210> SEQ ID NO 55
<211> LENGTH: 22
<212> TYPE: RNA
<213> ORGANISM: Homo sapiens

<400> SEQUENCE: 55
cagugcaaug uuaaagggc au                                           22

<210> SEQ ID NO 56
<211> LENGTH: 23
<212> TYPE: RNA
<213> ORGANISM: Homo sapiens

<400> SEQUENCE: 56
agguucugug auacacuccg acu                                         23

<210> SEQ ID NO 57
<211> LENGTH: 21
<212> TYPE: RNA
<213> ORGANISM: Homo sapiens

<400> SEQUENCE: 57
uucacagugg cuaaguucug c                                           21

<210> SEQ ID NO 58
<211> LENGTH: 23
<212> TYPE: RNA
<213> ORGANISM: Homo sapiens

<400> SEQUENCE: 58
cagugcaaua guauugucaa agc                                         23

<210> SEQ ID NO 59
<211> LENGTH: 20
<212> TYPE: RNA
<213> ORGANISM: Homo sapiens

<400> SEQUENCE: 59
ccucugggcc cuuccuccag                                             20

<210> SEQ ID NO 60
<211> LENGTH: 22
<212> TYPE: RNA
<213> ORGANISM: Homo sapiens
```

-continued

```
<400> SEQUENCE: 60
gcugacuccu aguccagggc uc                                              22

<210> SEQ ID NO 61
<211> LENGTH: 22
<212> TYPE: RNA
<213> ORGANISM: Homo sapiens

<400> SEQUENCE: 61
uuaucagaau cuccaggggu ac                                              22

<210> SEQ ID NO 62
<211> LENGTH: 22
<212> TYPE: RNA
<213> ORGANISM: Homo sapiens

<400> SEQUENCE: 62
acuggacuua gggucagaag gc                                              22

<210> SEQ ID NO 63
<211> LENGTH: 23
<212> TYPE: RNA
<213> ORGANISM: Homo sapiens

<400> SEQUENCE: 63
uucauuuggu auaaaccgcg auu                                             23

<210> SEQ ID NO 64
<211> LENGTH: 22
<212> TYPE: RNA
<213> ORGANISM: Homo sapiens

<400> SEQUENCE: 64
gucccucucc aaaugugucu ug                                              22

<210> SEQ ID NO 65
<211> LENGTH: 22
<212> TYPE: RNA
<213> ORGANISM: Homo sapiens

<400> SEQUENCE: 65
aacccguaga uccgaucuug ug                                              22

<210> SEQ ID NO 66
<211> LENGTH: 22
<212> TYPE: RNA
<213> ORGANISM: Homo sapiens

<400> SEQUENCE: 66
aaagugcuuc ucuuuggugg gu                                              22

<210> SEQ ID NO 67
<211> LENGTH: 21
<212> TYPE: RNA
<213> ORGANISM: Homo sapiens

<400> SEQUENCE: 67
uggguuuacg uugggagaac u                                               21

<210> SEQ ID NO 68
<211> LENGTH: 21
<212> TYPE: RNA
```

```
<213> ORGANISM: Homo sapiens

<400> SEQUENCE: 68
aucacauugc cagggauuuc c                                               21

<210> SEQ ID NO 69
<211> LENGTH: 22
<212> TYPE: RNA
<213> ORGANISM: Homo sapiens

<400> SEQUENCE: 69
ucagugcauc acagaacuuu gu                                              22
```